US012337159B1

(12) United States Patent
Hee-Hanson et al.

(10) Patent No.: US 12,337,159 B1
(45) Date of Patent: Jun. 24, 2025

(54) MEDICAMENT DELIVERY DEVICE

(71) Applicant: Genzyme Corporation, Cambridge, MA (US)

(72) Inventors: Alexander Hee-Hanson, Melbourn (GB); Thomas Lever, Melbourn (GB); Michael Parrott, Melbourn (GB); Robert Wilson, Melbourn (GB)

(73) Assignee: Genzyme Corporation, Cambridge, MA (US)

( * ) Notice: Subject to any disclaimer, the term of this patent is extended or adjusted under 35 U.S.C. 154(b) by 0 days.

(21) Appl. No.: 18/815,336

(22) Filed: Aug. 26, 2024

Related U.S. Application Data

(63) Continuation of application No. 18/594,597, filed on Mar. 4, 2024.

(51) Int. Cl.
*A61M 5/32* (2006.01)
*A61M 5/20* (2006.01)

(52) U.S. Cl.
CPC ........ *A61M 5/3245* (2013.01); *A61M 5/2033* (2013.01); *A61M 5/3257* (2013.01);
(Continued)

(58) Field of Classification Search
CPC .................................................. A61M 5/3257
See application file for complete search history.

(56) References Cited

U.S. PATENT DOCUMENTS 4,915,701 A * 4/1990 Halkyard ............ A61M 5/3271
604/232
5,356,387 A * 10/1994 Sirbola ............... A61M 5/3275
604/263
(Continued)

FOREIGN PATENT DOCUMENTS

CH 705345 A2 2/2013
CH 705992 A2 6/2013
(Continued)

OTHER PUBLICATIONS

Needle-based injection systems for medical use Requirements and test methods, Part 1: Needle injection systems, ISO 11608 1:2014(E), Third Edition, Switzerland, ISO, Dec. 15, 2014, pp. 1-13.
(Continued)

*Primary Examiner* — Bradley J Osinski
(74) *Attorney, Agent, or Firm* — Fish & Richardson P.C.

(57) ABSTRACT

A medicament delivery device includes a needle disposed at a distal end of the medicament delivery device, a body for a syringe, and a needle cover axially movable relative to the body between an extended position in which the needle cover covers the needle and a retracted position for dispensing medicament from the medicament delivery device. The needle protruding from the distal end of the needle cover when the needle cover is in the retracted position. The medicament delivery device includes an actuation member configured to be movable from an initial position to an engaged position such that when the actuation member is in its initial position, the needle cover can be axially moved between its retracted position and its extended position, and when the actuation member is in its engaged position, the actuation member engages with the needle cover to hold the needle cover in its retracted position.

29 Claims, 18 Drawing Sheets

(52) U.S. Cl.
CPC ............... *A61M 2005/2013* (2013.01); *A61M 2005/206* (2013.01); *A61M 2005/208* (2013.01)

(56) References Cited

U.S. PATENT DOCUMENTS

| | | |
|---|---|---|
| 7,597,685 B2 | 10/2009 | Olson |
| 8,048,035 B2 | 11/2011 | Mesa et al. |
| 8,945,063 B2 | 2/2015 | Wotton et al. |
| 9,216,256 B2 | 12/2015 | Olson et al. |
| 9,687,607 B2 | 6/2017 | Brereton et al. |
| 10,569,019 B2 | 2/2020 | Hirschel et al. |
| 10,799,647 B2 | 10/2020 | Hostettler et al. |
| 11,116,911 B2 | 9/2021 | Wu |
| 11,383,044 B2 | 7/2022 | Tschirren et al. |
| 2004/0039336 A1 | 2/2004 | Amark et al. |
| 2005/0101919 A1 | 5/2005 | Brunnberg |
| 2007/0060840 A1 | 3/2007 | Conway |
| 2007/0112310 A1 | 5/2007 | Lavi et al. |
| 2007/0239117 A1 | 10/2007 | Chelak et al. |
| 2013/0289525 A1 | 10/2013 | Kemp et al. |
| 2017/0106146 A1 | 4/2017 | Folk et al. |
| 2019/0358400 A1 | 11/2019 | Nakamura et al. |
| 2020/0046909 A1 | 2/2020 | Hommann et al. |
| 2020/0289754 A1 | 9/2020 | Liscio et al. |
| 2021/0361881 A1 | 11/2021 | Garson et al. |
| 2021/0393886 A1 | 12/2021 | Nicolas et al. |

FOREIGN PATENT DOCUMENTS

| | | |
|---|---|---|
| EP | 3381490 B1 | 9/2020 |
| WO | WO 2002/047746 A1 | 6/2002 |
| WO | WO 2010/136077 A1 | 12/2010 |
| WO | WO 2018/011417 A1 | 1/2018 |
| WO | WO 2021/160540 A1 | 8/2021 |
| WO | WO 2021/197804 A1 | 10/2021 |
| WO | WO 2022/069617 A1 | 4/2022 |
| WO | WO 2022/184388 A1 | 9/2022 |
| WO | WO 2022/223789 A1 | 10/2022 |
| WO | WO 2023/057578 A1 | 4/2023 |

OTHER PUBLICATIONS

U.S. Appl. No. 18/594,556, filed Mar. 4, 2024, Alexander Hee-Hanson.

U.S. Appl. No. 18/594,683, filed Mar. 4, 2024, Alexander Hee-Hanson.

U.S. Appl. No. 18/594,643, filed Mar. 4, 2024, Alexander Hee-Hanson.

* cited by examiner

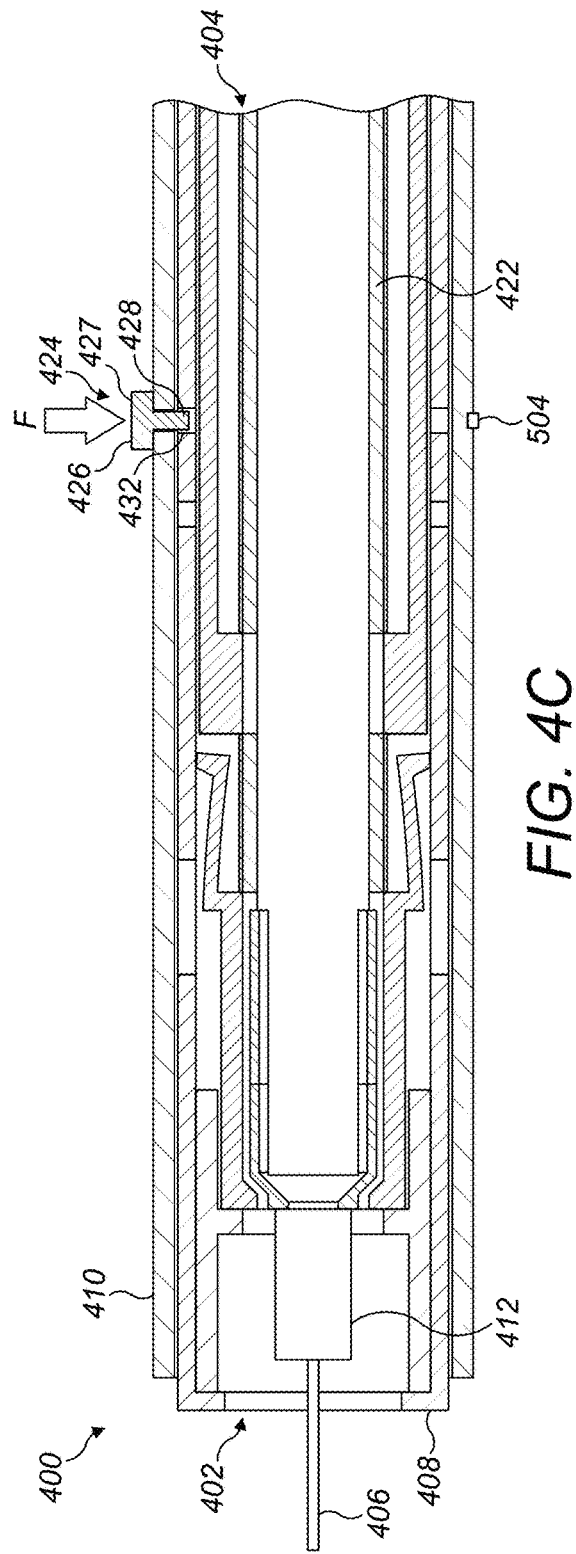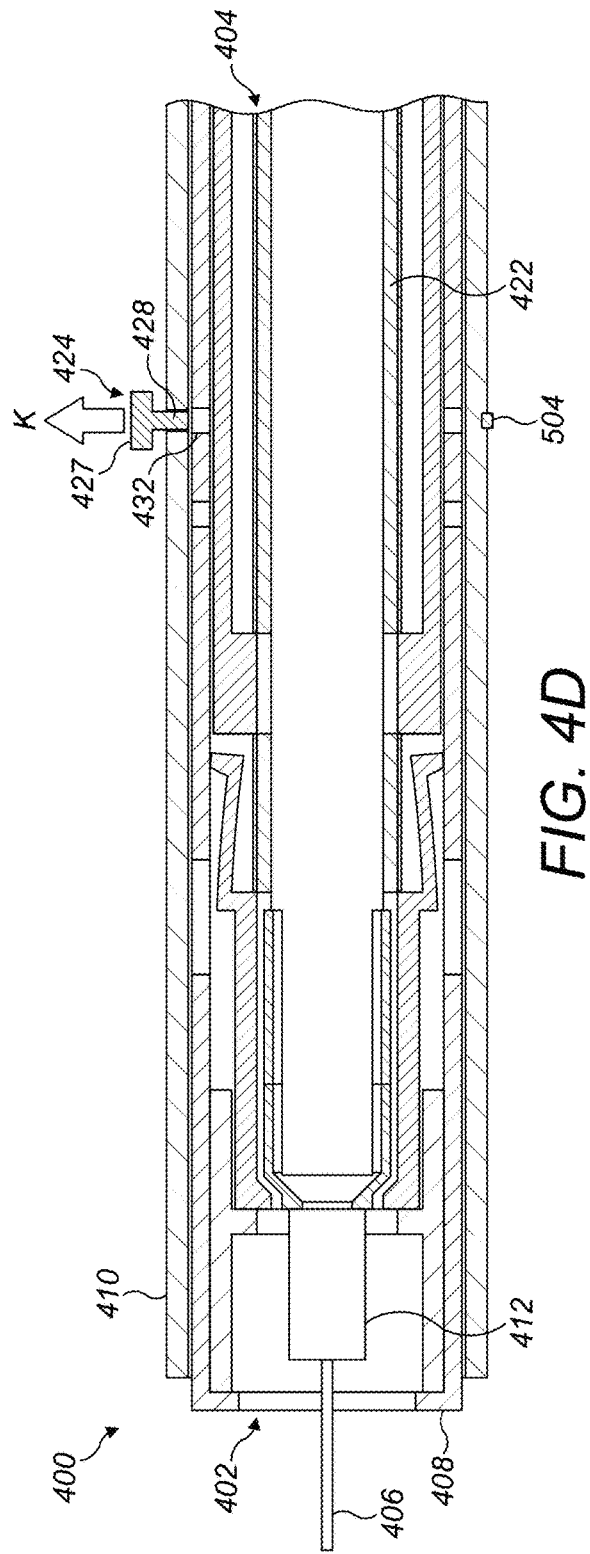

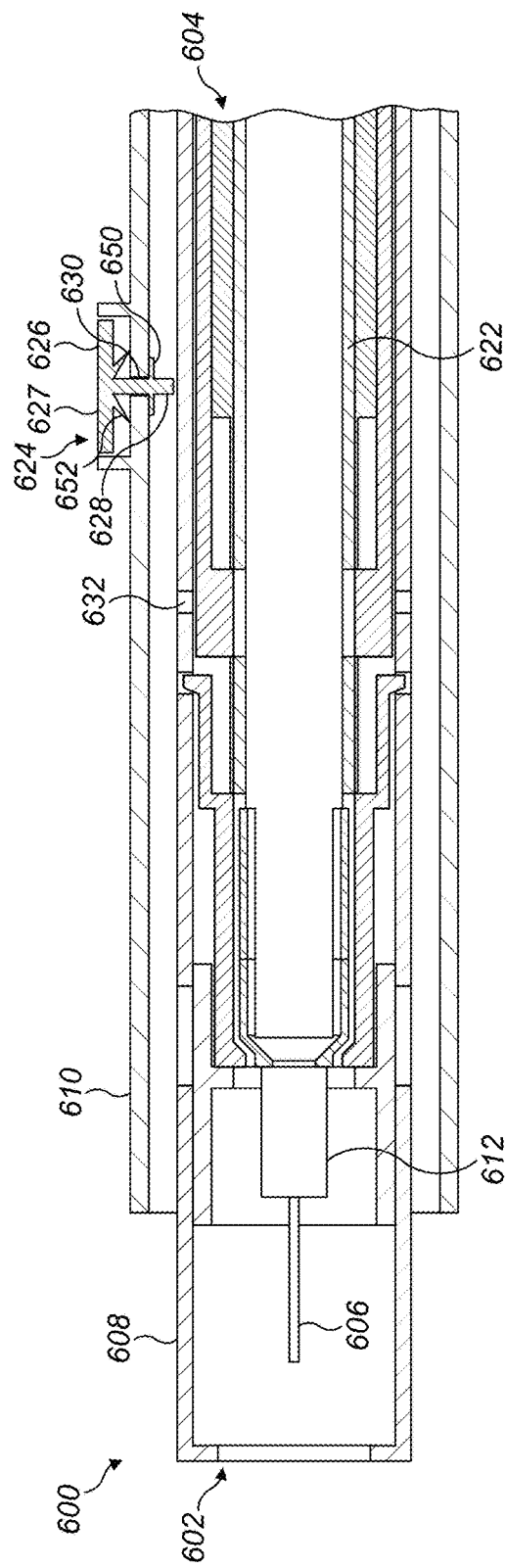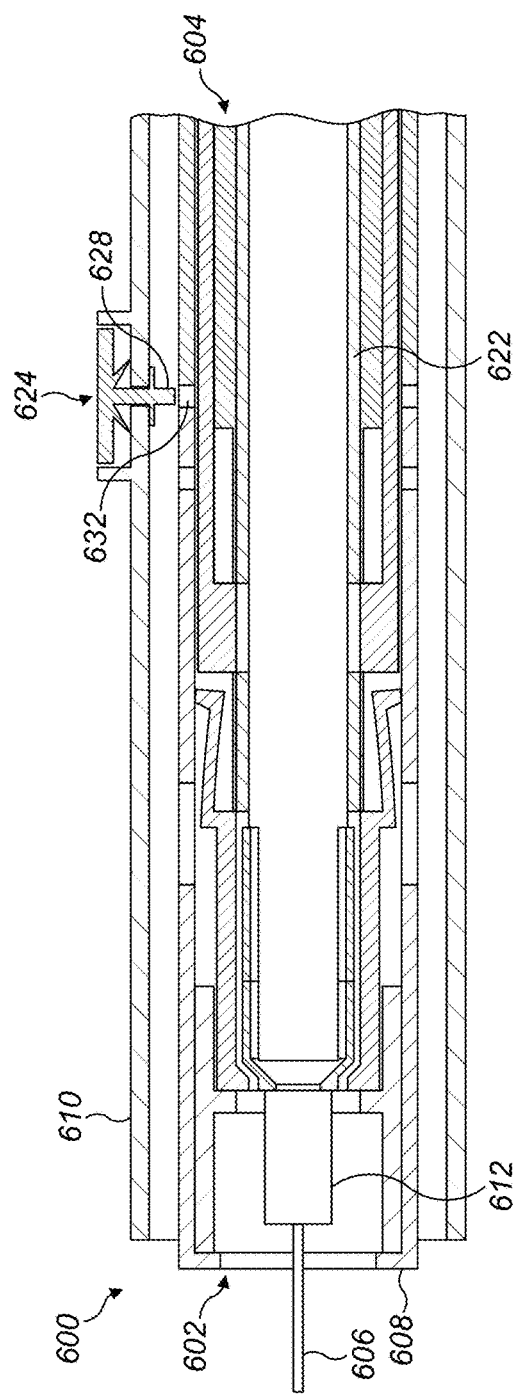

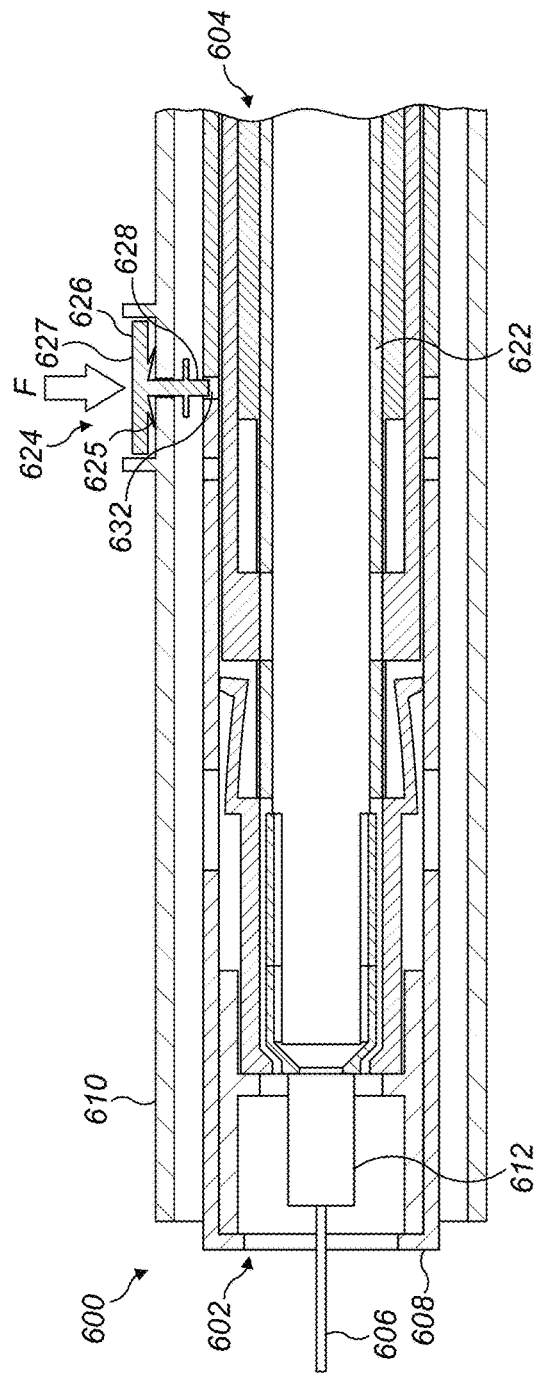
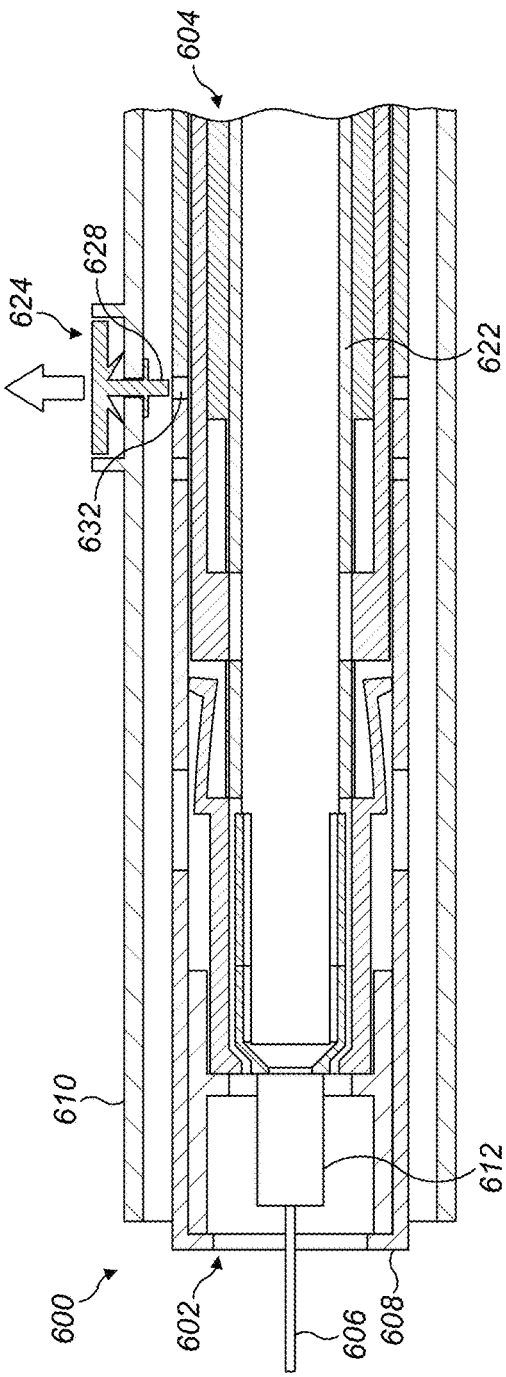
FIG. 6C
FIG. 6D

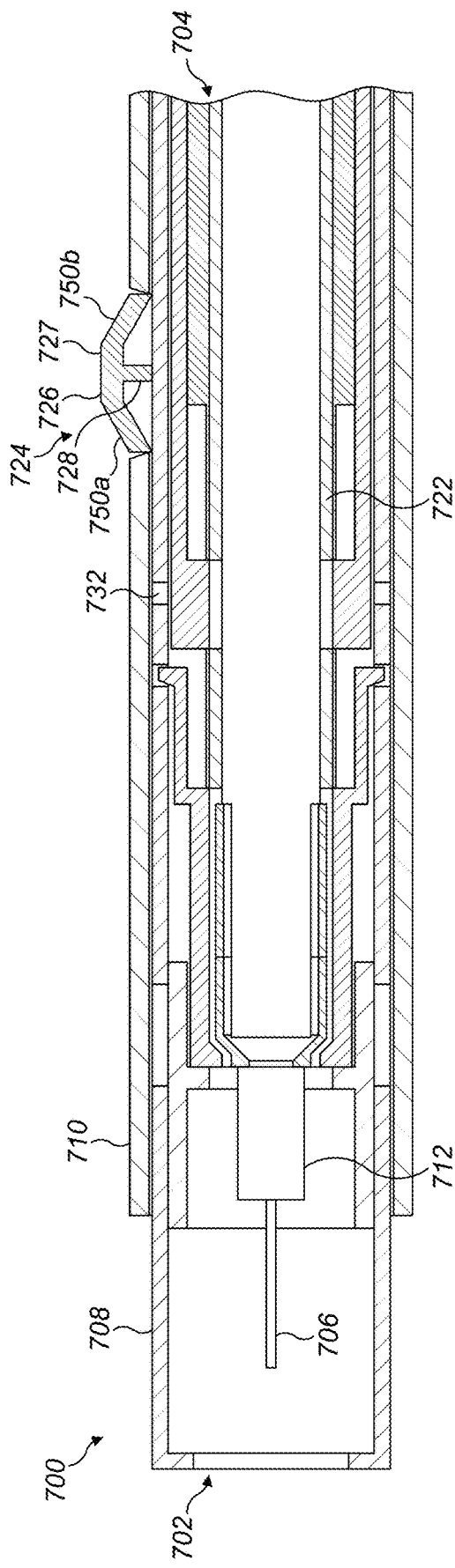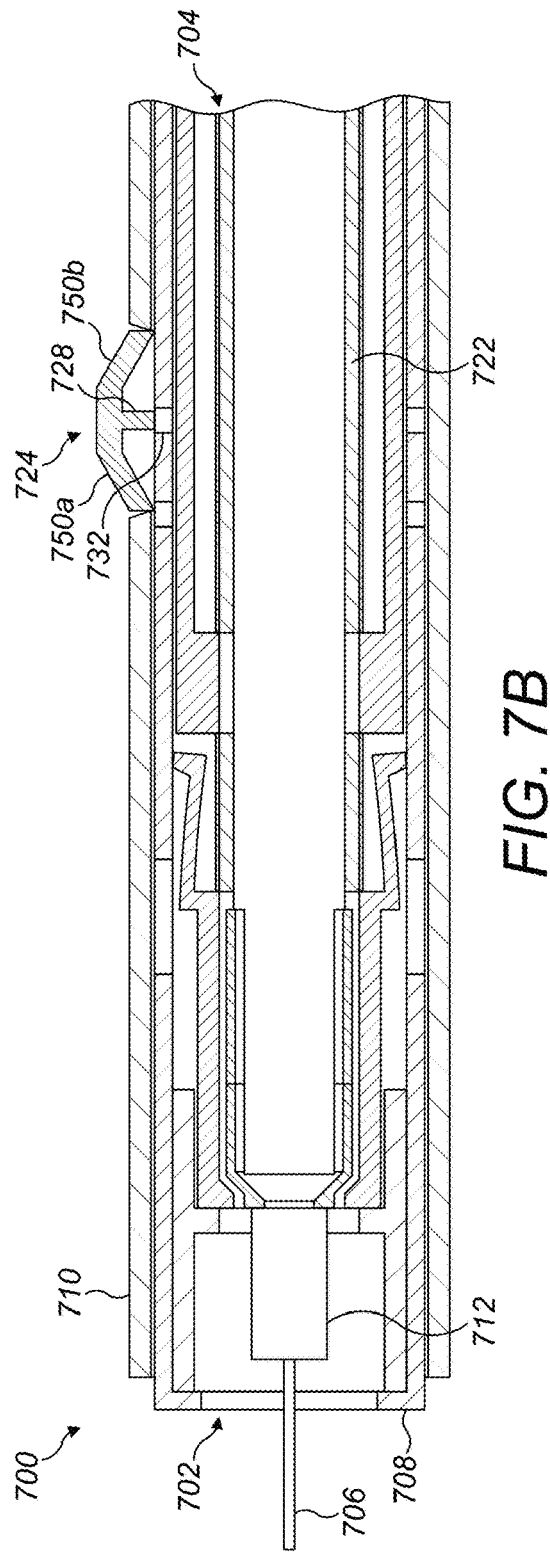
FIG. 7A
FIG. 7B

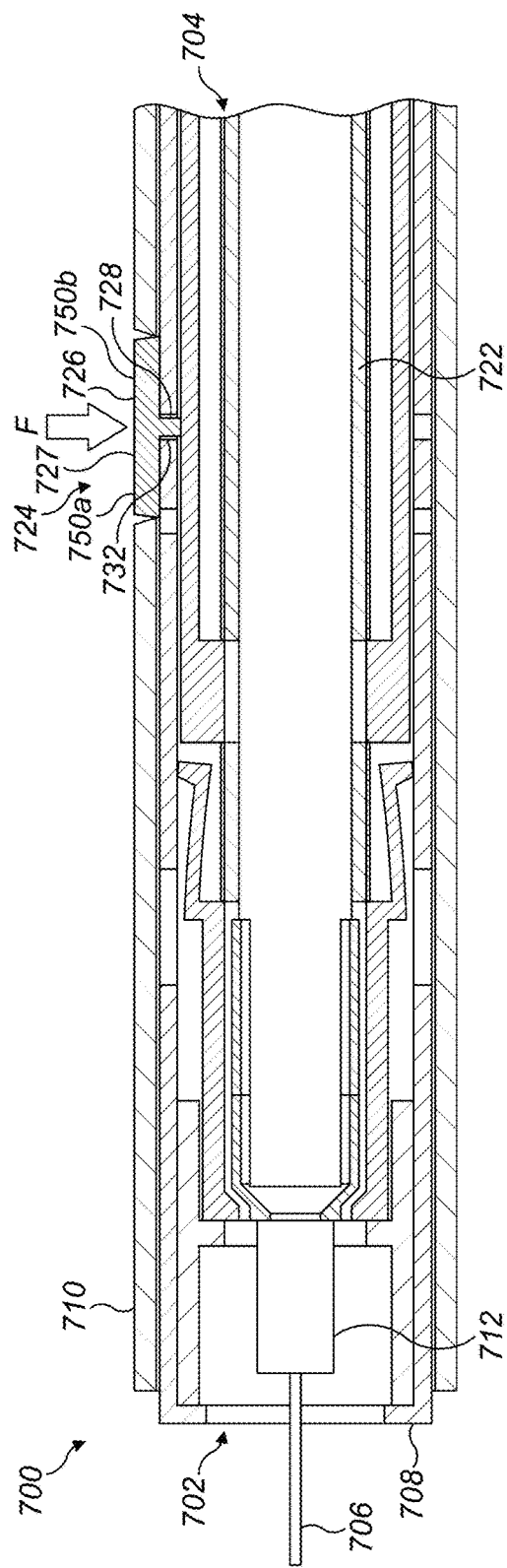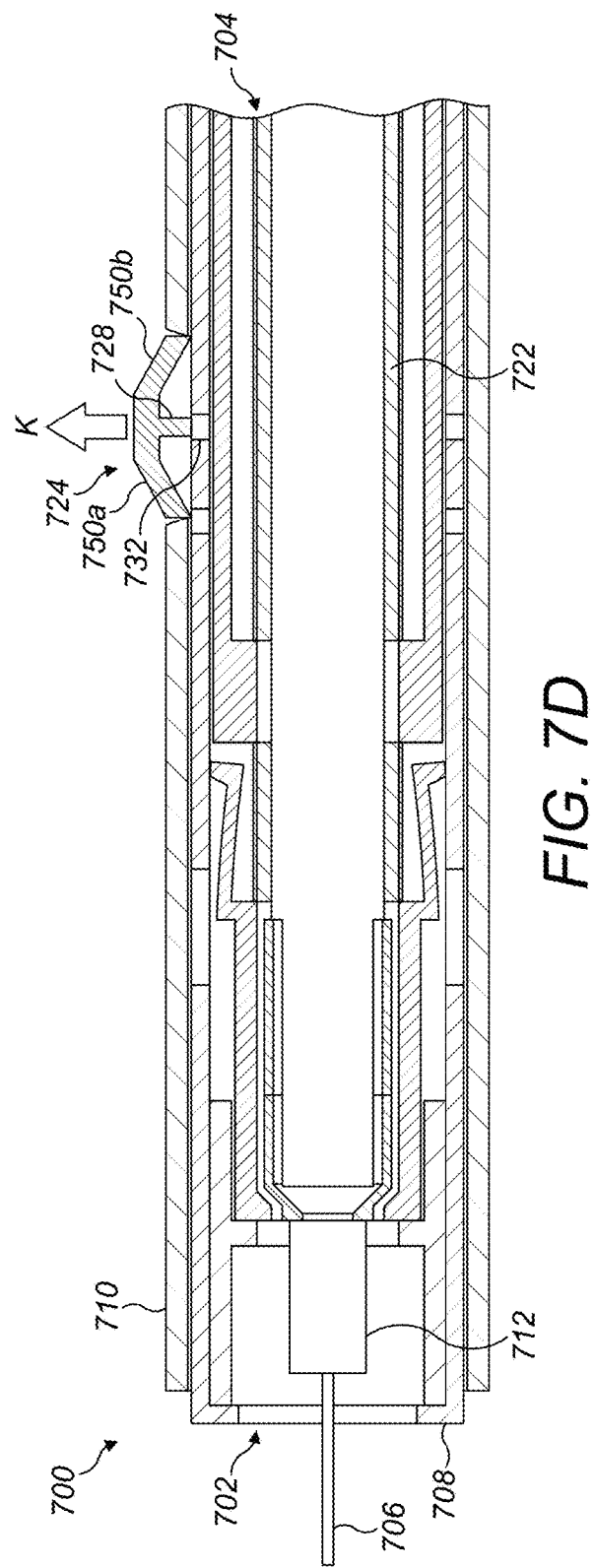

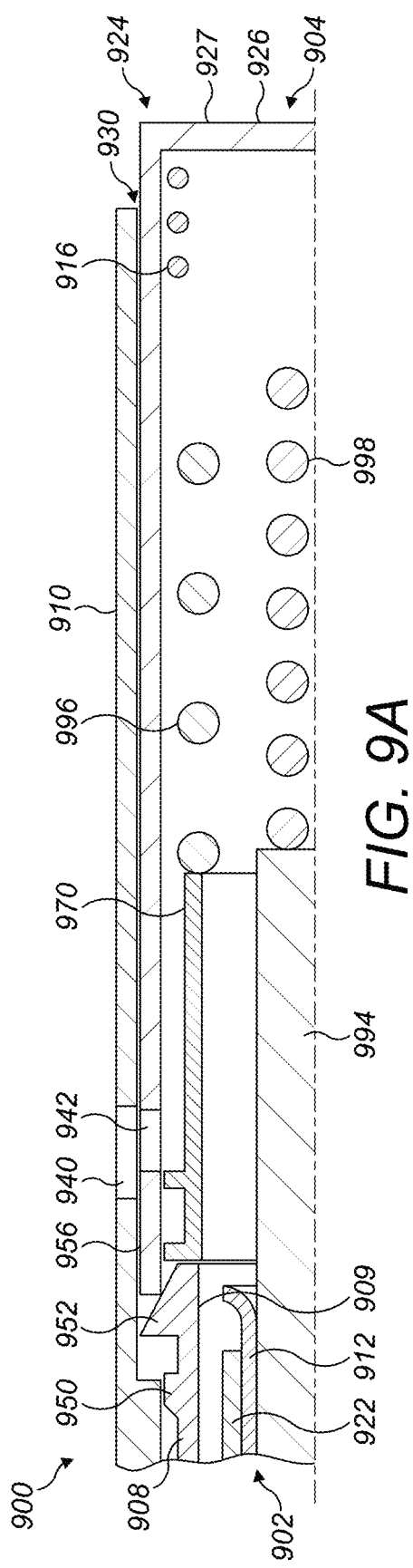
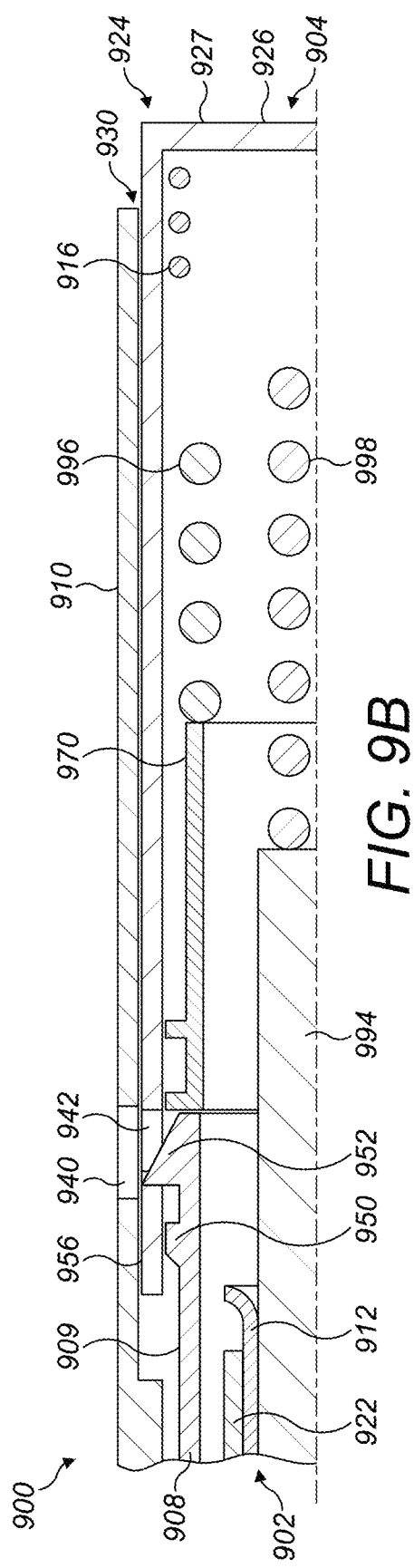
FIG. 9A
FIG. 9B

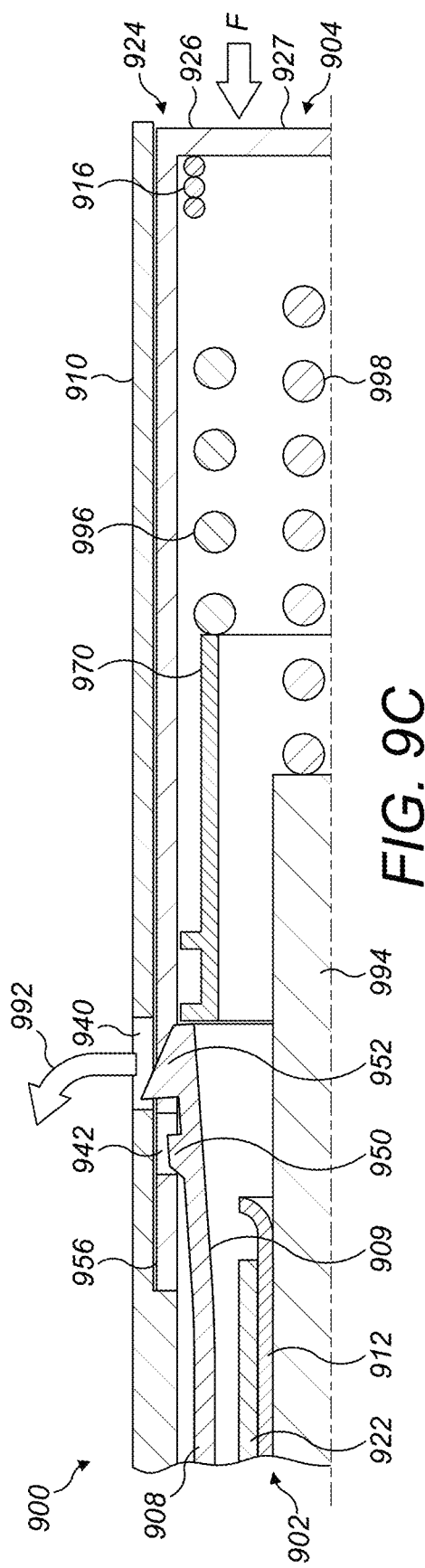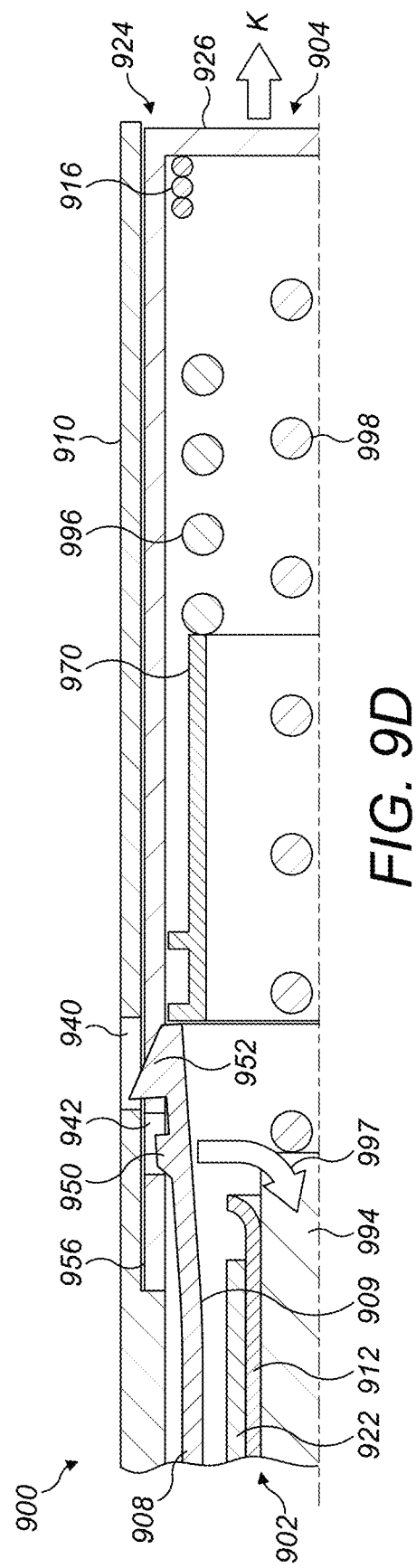

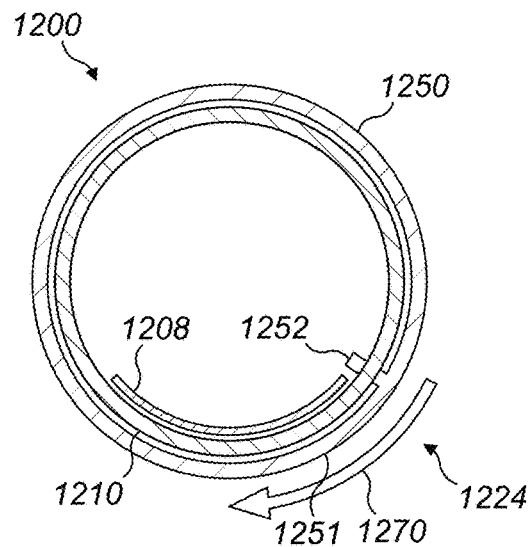
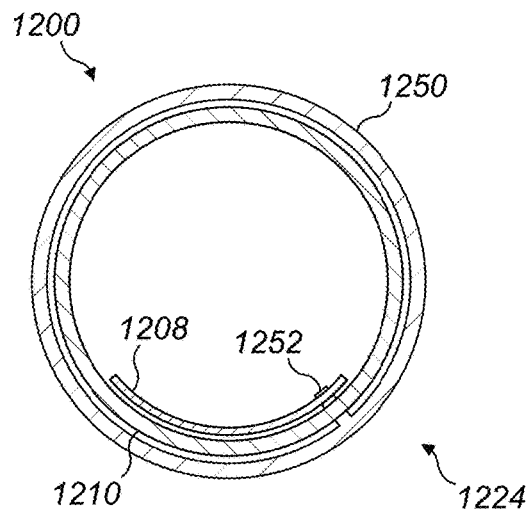
FIG. 12A
FIG. 12B
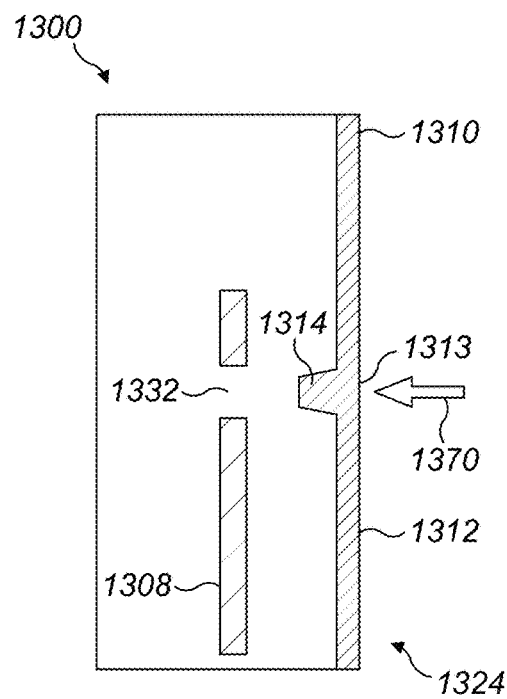
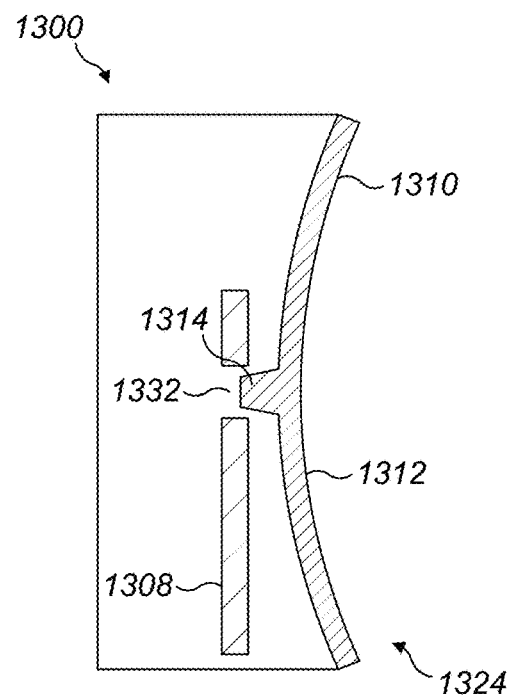
FIG. 13A
FIG. 13B

MEDICAMENT DELIVERY DEVICE

CROSS REFERENCE TO RELATED APPLICATION

The present application is a continuation of U.S. patent application Ser. No. 18/594,597, filed Mar. 4, 2024.

TECHNICAL FIELD

This application relates to a medicament delivery device for delivery of a medicament, for example an injector device such as an auto-injector device.

BACKGROUND

Injector devices are used to deliver a range of medicaments. In an auto-injector device, some or all of the actions required to use the injector device in administering medicament to a user are automated.

It is known to provide an auto-injector device having a needle cover which is axially movable to cover and uncover a needle, with the needle cover being biased by a spring to extend over the needle. Typically, the user presses the needle cover against an injection site, against the force of the spring, to push the needle cover into the housing and to uncover the needle which is pushed into the injection site. Medicament is automatically dispensed from the needle via an automated mechanism. A user typically holds the needle cover in a holding position for a predetermined period of time, to ensure that the correct dose of medicament is dispensed from the device, before removing the device from the injection site.

Some users find it difficult to fully depress the needle cover due to the force required or the change in force experienced during the activation movement. This may result in the needle not entering the user's skin to the correct depth, pain, discomfort, a wet injection site, early device removal and/or partial delivery of the medicament.

SUMMARY

A first aspect of this disclosure provides a medicament delivery device comprising:
- a needle for injecting medicament into a user, the needle disposed at a distal end of the medicament delivery device;
- a body for containing a pre-filled syringe;
- a needle cover axially movable relative to the body between an extended position, in which the needle cover covers the needle, and a retracted position for dispensing medicament from the medicament delivery device, wherein the needle protrudes from the distal end of the needle cover when the needle cover is in the retracted position; and
- an actuation member configured to be movable by the user from an initial position to an engaged position,
- wherein, when the actuation member is in its initial position, the needle cover can be axially moved between its retracted position and its extended position, and
- wherein, when the actuation member is in its engaged position, the actuation member engages with the needle cover to hold the needle cover in its retracted position.

The medicament delivery device may further comprise a biasing member configured to bias the actuation member from its engaged position to its initial position.

The actuation member may be configured to be moved from its initial position to its engaged position by the user applying an actuation force to an outer surface of the actuation member.

The actuation member may comprise a button arranged at an outer surface of the body.

The actuation member may comprise a protrusion; the needle cover may comprise a cooperating element; the protrusion may be engaged with the cooperating element when the actuation member is in its engaged position to hold the needle cover in its retracted position; and the protrusion may be disengaged from the cooperating element when the actuation member is in its initial position such that the needle cover can be axially moved between its retracted position and its extended position.

The protrusion may be configured to engage a distal-facing side of the cooperating element when the actuation member is in its engaged position to hold the needle cover in its retracted position.

The needle cover may comprise a resilient member for engaging with a cooperating element of the medicament delivery device, and the actuation member, when moved from its initial position to its engaged position, may be configured to cause the resilient member to be deflected such that the resilient member engages the cooperating element to hold the needle cover in its retracted position.

The resilient member may comprise a flexible arm and a protrusion disposed on a free end of the flexible arm; the actuation member may comprise an elongate arm; and the elongate arm may be configured to push the flexible arm when the actuation member is moved from its initial position to its engaged position, to cause the flexible arm to deflect such that the protrusion engages the cooperating element to hold the needle cover in its retracted position.

The resilient member may comprise a flexible arm and a protrusion disposed on a free end of the flexible arm; the actuation member may comprise an elongate arm; the body may comprise the cooperating element; the flexible arm may be movable between a first position, in which the protrusion engages the cooperating element to hold the needle cover in its retracted position, and a second position, in which the protrusion is disengaged from the cooperating element; the flexible arm may be biased to deflect from its second position to its first position; the elongate arm may be configured to hold the flexible arm in its second position when the actuation member is in its initial position; and the elongate arm may be configured to release the flexible arm to deflect to its first position when the actuation member is in its engaged position.

The actuation member comprises a slider, the slider comprising: a slider body arranged at an outer surface of the body; a resilient arm extending from the slider body through an aperture in the body; and a protrusion disposed at a free end of the resilient arm between an inner surface of the body and an outer surface of the needle cover, wherein the actuation member is configured to be moved from its initial position to its engaged position by a user sliding the slider body towards the aperture in the body such that the resilient arm is deflected by an edge of the aperture to cause the protrusion to engage a cooperating element disposed on the needle cover to hold the needle cover in its retracted position.

The actuation member may comprise a pivotable arm arranged to extend through an aperture in the body, the pivotable arm comprising: a first arm portion arranged outside the body; a second arm portion arranged inside the body and having a protrusion disposed at a free end of the second arm portion; and a pivot arranged between the first arm portion and the second arm portion, wherein the actuation member is configured to be moved from its initial position to its engaged position by a user applying an actuation force to the first arm portion to cause the first arm portion and the second arm portion to rotate about the pivot such that the protrusion disposed at the free end of the second arm portion is brought into engagement with a cooperating element disposed on the needle cover to hold the needle cover in its retracted position.

The actuation member may comprise a rotatable collar arranged to surround an outer surface of the body, the rotatable collar comprising a protrusion disposed on an inner surface of the rotatable collar, the protrusion extending through an aperture in the body, wherein the actuation member is configured to be moved from its initial position to its engaged position by a user rotating the rotatable collar about the body such that the protrusion is brought into engagement with a cooperating element disposed on the needle cover to hold the needle cover in its retracted position.

The actuation member may comprise a resilient portion of the body and a protrusion formed on an inner surface of the resilient portion of the body, wherein the actuation member is configured to be moved from its initial position to its engaged position by a user applying an actuation force to an outer surface of the resilient portion of the body such that the resilient portion of the body is deflected to cause the protrusion to engage a cooperating element disposed on the needle cover to hold the needle cover in its retracted position.

The medicament delivery device may further comprise a needle cover biasing member configured to exert a force which biases the needle cover axially, towards the distal end of the medicament delivery device.

The medicament delivery device may further comprise the pre-filled syringe.

A second aspect of this disclosure provides a medicament delivery device comprising:
  a body for containing a pre-filled syringe;
  a needle cover axially movable relative to the body between an extended position, in which the needle cover covers a needle coupled to the pre-filled syringe, and a retracted position, in which the needle protrudes from a distal end of the needle cover; and
  a button configured to be actuated by a user to hold the needle cover in its retracted position.

The button may be configured to be actuated such that it moves from an initial position, in which the needle cover can be axially moved between its retracted position and its extended position, to an engaged position, in which the button holds the needle cover in its retracted position.

The medicament delivery device may further comprise a biasing member configured to bias the button from its engaged position to its initial position.

The button may be configured to be actuated by the user applying an actuation force to an outer surface of the button.

The button may be arranged at an outer circumferential surface of the body and actuation of the button may cause the button to move radially into the body to hold the needle cover.

The button may be arranged to extend through an opening at a proximal end face of the body and actuation of the button may cause the button to move axially into the body to hold the needle cover.

The button may be integrally formed with the body.

The needle cover may be arranged to prevent the button from being actuated when the needle cover is in its extended position, and the needle cover may be arranged to allow the button to be actuated when the needle cover is in its extended position The button may comprise a protrusion, the needle cover may comprise a cooperating element, and actuation of the button may cause the protrusion to engage the cooperating element to hold the needle cover in its retracted position.

The cooperating element may comprise an aperture, a recess, a ridge or a frictional surface.

The needle cover may comprise a resilient member for engaging with a cooperating element of the medicament delivery device, wherein actuation of the button causes the resilient member to be deflected such that the resilient member engages the cooperating element to hold the needle cover in its retracted position.

The resilient member may comprise a flexible arm and a protrusion disposed on a free end of the flexible arm, the button may comprise an elongate arm, and actuation of the button may cause the elongate arm to deflect the flexible arm such that the protrusion engages the cooperating element to hold the needle cover in its retracted position.

The resilient member may comprise a flexible arm and a protrusion disposed on a free end of the flexible arm; the button may comprise an elongate arm; the body may comprise the cooperating element; the flexible arm may be movable between a first position, in which the protrusion engages the cooperating element to hold the needle cover in its retracted position, and a second position, in which the protrusion is disengaged from the cooperating element; the flexible arm may be biased to deflect from its second position to its first position; the elongate arm may be configured to hold the flexible arm in its second position prior to actuation of the button; and actuation of the button may cause the elongate arm to release the flexible arm to deflect to its first position.

The medicament delivery device may further comprise a needle cover biasing member configured to exert a force to bias the needle cover from its retracted position to its extended position.

The medicament delivery device may further comprise the pre-filled syringe.

BRIEF DESCRIPTION OF THE DRAWINGS

Exemplary embodiments are described with reference to the accompanying drawings, in which:

FIG. 4C shows the medicament delivery device of FIG. 4B with the actuation member in an engaged position;

FIG. 4D shows the medicament delivery device of FIG. 4C with the actuation member having returned to the initial position;

FIG. 6A shows a medicament delivery device according to a third embodiment in an initial state;

FIG. 6B shows the medicament delivery device of FIG. 6A in an activated state, with the actuation member in an initial position;

FIG. 6C shows the medicament delivery device of FIG. 6B with the actuation member in an engaged position;

FIG. 6D shows the medicament delivery device of FIG. 6C with the actuation member having returned to the initial position;

FIG. 7A shows a medicament delivery device according to a fourth embodiment in an initial state;

FIG. 7B shows the medicament delivery device of FIG. 7A in an activated state, with the actuation member in an initial position;

FIG. 7C shows the medicament delivery device of FIG. 7B with the actuation member in an engaged position;

FIG. 7D shows the medicament delivery device of FIG. 7C with the actuation member having returned to the initial position;

FIG. 9A shows a medicament delivery device according to a sixth embodiment in an initial state;

FIG. 9B shows the medicament delivery device of FIG. 9A in an activated state, with the actuation member in an initial position;

FIG. 9C shows the medicament delivery device of FIG. 9B with the actuation member in an engaged position;

FIG. 9D shows the medicament delivery device of FIG. 9C with the actuation member having returned to the initial position;

FIG. 12A shows portions of a medicament delivery device according to a ninth embodiment with an actuation member in an initial position;

FIG. 12B shows portions of the medicament delivery device of FIG. 12A with the actuation member in an engaged position; and FIG. 13A shows portions of a medicament delivery device according to a tenth embodiment with an actuation member in an initial position;

FIG. 13B shows portions of the medicament delivery device of FIG. 13A with the actuation member in an engaged position.

DETAILED DESCRIPTION

Figure 1A:
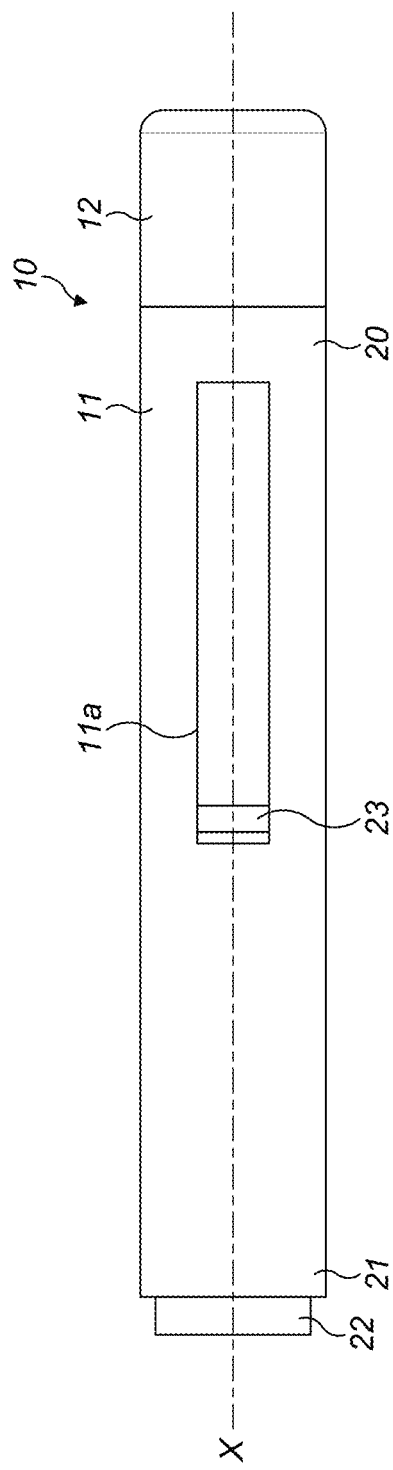
FIG. 1A shows an injector device with a cap attached.

A drug delivery device (also referred to as a medicament delivery device), as described herein, may be configured to inject a medicament into a patient. For example, delivery could be sub-cutaneous, intra-muscular, or intravenous. Such a device could be operated by a patient or care-giver, such as a nurse or physician, and can include various types of safety syringe, pen-injector, or auto-injector. The device can include a cartridge-based system that requires piercing a sealed ampule before use. Volumes of medicament delivered with these various devices can range from about 0.5 ml to about 2 ml. Yet another device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 10 ml).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 27 and 29 Gauge.

The delivery devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of an auto-injector may each be activated via an activation mechanism. Such an activation mechanism can include one or more of a button, a lever, a needle sleeve, or other activation component. Activation of an automated function may be a one-step or multi-step process. That is, a user may need to activate one or more activation components in order to cause the automated function. For example, in a one-step process, a user may depress a needle sleeve against their body in order to cause injection of a medicament. Other devices may require a multi-step activation of an automated function. For example, a user may be required to depress a button and retract a needle shield in order to cause injection.

In addition, activation of one automated function may activate one or more subsequent automated functions, thereby forming an activation sequence. For example, activation of a first automated function may activate at least two of needle insertion, medicament injection, and needle retraction. Some devices may also require a specific sequence of steps to cause the one or more automated functions to occur. Other devices may operate with a sequence of independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

Figure 1B:
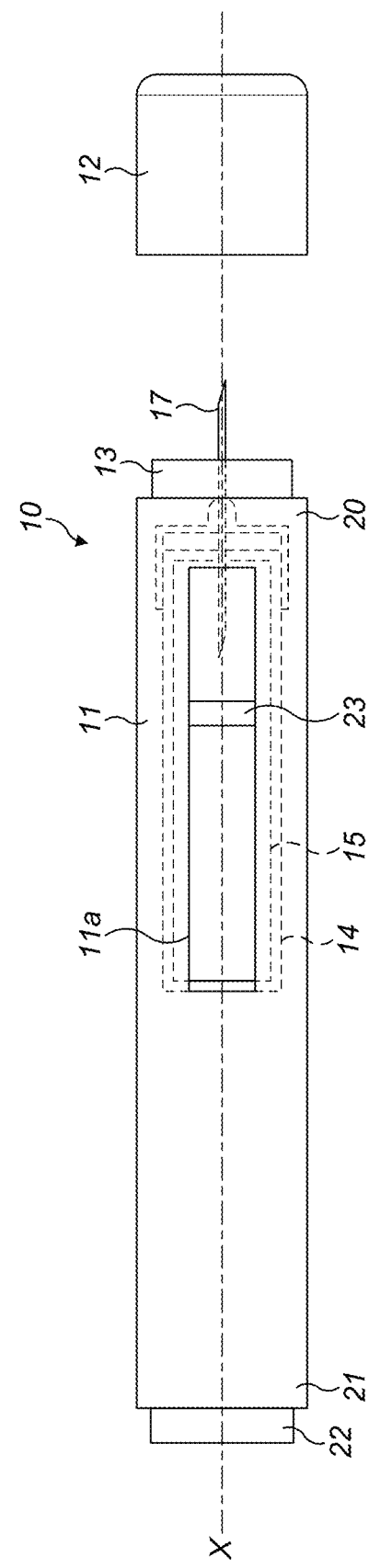
FIG. 1B shows the injector device of FIG. 1A with the cap removed.

According to some embodiments of the present disclosure, an exemplary drug delivery device 10 is shown in FIGS. 1A & 1B. Device 10, as described above, is configured to inject a medicament 15 into a patient's body. Device 10 includes a housing 11 which typically contains a reservoir 14 containing the medicament 15 to be injected (e.g., a syringe) and the components required to facilitate one or more steps of the delivery process. Device 10 can also include a cap assembly 12 that can be detachably mounted to the housing 11. Typically, a user removes cap 12 from housing 11 before device 10 can be operated. Device 10 can include a window 11a through which a user may view medicament 15 remaining in the reservoir 14.

As shown, housing 11 is substantially cylindrical and has a substantially constant diameter along the longitudinal axis X of the device 10. The housing 11 has a distal region 20 and a proximal region 21. The term "distal" refers to a location that is relatively closer to a site of injection, and the term "proximal" refers to a location that is relatively further away from the injection site.

Device 10 can also include a needle sleeve 13 coupled to housing 11 to permit movement of sleeve 13 relative to housing 11. For example, sleeve 13 can move in a longitudinal direction parallel to longitudinal axis X. Specifically, movement of sleeve 13 in a proximal direction can permit a needle 17 to extend from distal region 20 of housing 11.

Insertion of needle 17 can occur via several mechanisms. For example, needle 17 may be fixedly located relative to housing 11 and initially be located within an extended needle sleeve 13. Proximal movement of sleeve 13 by placing a distal end of sleeve 13 against an injection site such as a patient's body and moving housing 11 in a distal direction will uncover the distal end of needle 17. Such relative movement allows the distal end of needle 17 to extend into the patient's body. Such insertion is termed "manual" insertion as needle 17 is manually inserted via the patient's manual movement of housing 11 relative to sleeve 13.

Another form of insertion is "automated," whereby needle 17 moves relative to housing 11. Such insertion can be triggered by movement of sleeve 13 or by another form of activation, such as, for example, a button 22. As shown in FIGS. 1A & 1B, button 22 is located at a proximal end 21 of housing 11. However, in other embodiments, button 22 could be located on a side of housing 11.

Other manual or automated features can include drug injection or needle retraction, or both. Injection is the process by which a bung or piston 23 is moved from a proximal location within a syringe to a more distal location within the syringe in order to force a medicament 15 from the syringe through needle 17. In some embodiments, a drive spring is under compression before device 10 is activated. A proximal end of the drive spring can be fixed within proximal region 21 of housing 11, and a distal end of the drive spring can be configured to apply a compressive force to a proximal surface of piston 23. Following activation, at least part of the energy stored in the drive spring can be applied to the proximal surface of piston 23. This compressive force can act on piston 23 to move it in a distal direction. Such distal movement acts to compress the liquid medicament 15 within the syringe, forcing it out of needle 17.

Following injection, needle 17 can be retracted within sleeve 13 or housing 11. Retraction can occur when sleeve 13 moves distally as a user removes device 10 from a patient's body. This can occur as needle 17 remains fixedly located relative to housing 11. Once a distal end of sleeve 13 has moved past a distal end of needle 17, and needle 17 is covered, sleeve 13 can be locked. Such locking can include locking any proximal movement of sleeve 13 relative to housing 11.

Another form of needle retraction can occur if needle 17 is moved relative to housing 11. Such movement can occur if the syringe within housing 11 is moved in a proximal direction relative to housing 11. This proximal movement can be achieved by using a retraction spring, located in distal region 20. A compressed retraction spring, when activated, can supply sufficient force to the syringe to move it in a proximal direction. Following sufficient retraction, any relative movement between needle 17 and housing 11 can be locked with a locking mechanism. In addition, button 22 or other components of device 10 can be locked as required.

Figure 2A:
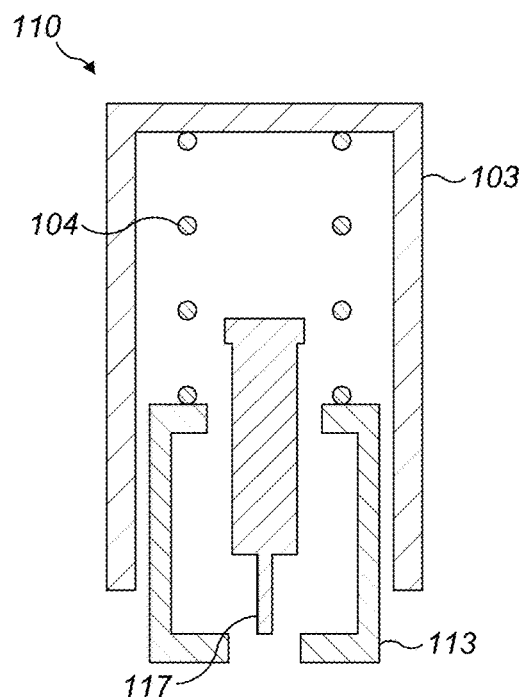
FIG. 2A shows a simplified view of a injector device prior to use.
Figure 2B:
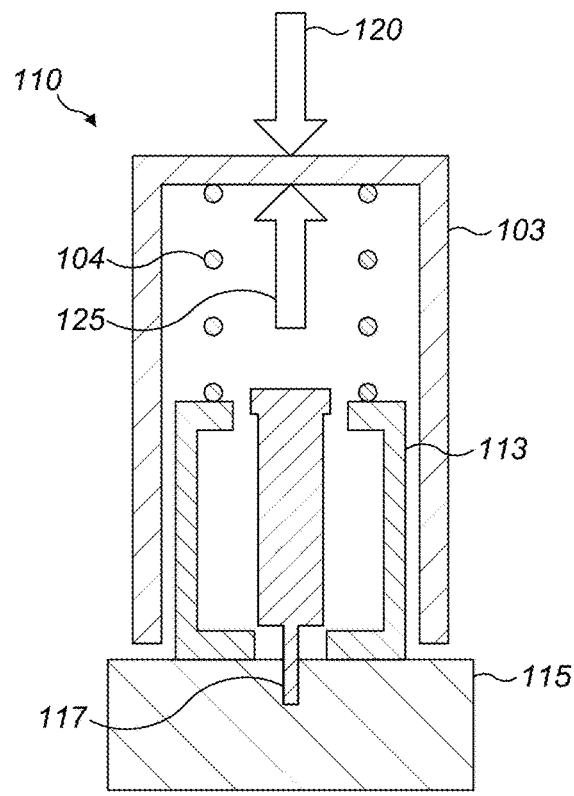
FIG. 2B shows a view of the device of FIG. 2A with injector device in the holding position.

FIGS. 2A and 2B show a simplified view of a device 110 having a needle cover 113 which is axially movable to cover and uncover the needle 117. The needle cover 113 is biased by a spring 104 to extend over the needle 117.

FIG. 2A shows the device before use, in which the needle cover 113 is exposed out of the end of the device body 103 and covers the needle 117. A force can be applied by a user against a spring force 125 to move the needle cover 113 from the position shown in FIG. 2A towards a holding position shown in FIG. 2B, and a holding force 120 can be applied to maintain the needle cover in the holding position.

Typically, the user presses the needle cover 113 against an injection site 115 to push the needle cover 113 at least partially into the device body 103. The exposed needle 117 is pushed into the injection site 115. In the holding position, medicament is automatically dispensed from the needle 117 via an automated mechanism. A user typically holds the needle cover 113 in the holding position for a predetermined period of time, to ensure that the correct dose of medicament is dispensed from the device 110, before removing the device from the injection site 115.

The spring force 125 against which the user applies a force to move the needle cover 113 is one component of the "activation force" of the device 110. The activation force refers to the force or force profile that the user exerts on the device 110 to move the needle cover 113 from the position shown in FIG. 2A to the position shown in FIG. 2B. If this force or force profile is not well balanced, it can lead to difficulty in activating the device 100 for some users, or increase the pain or anxiety associated with using the device.

Figure 3A:
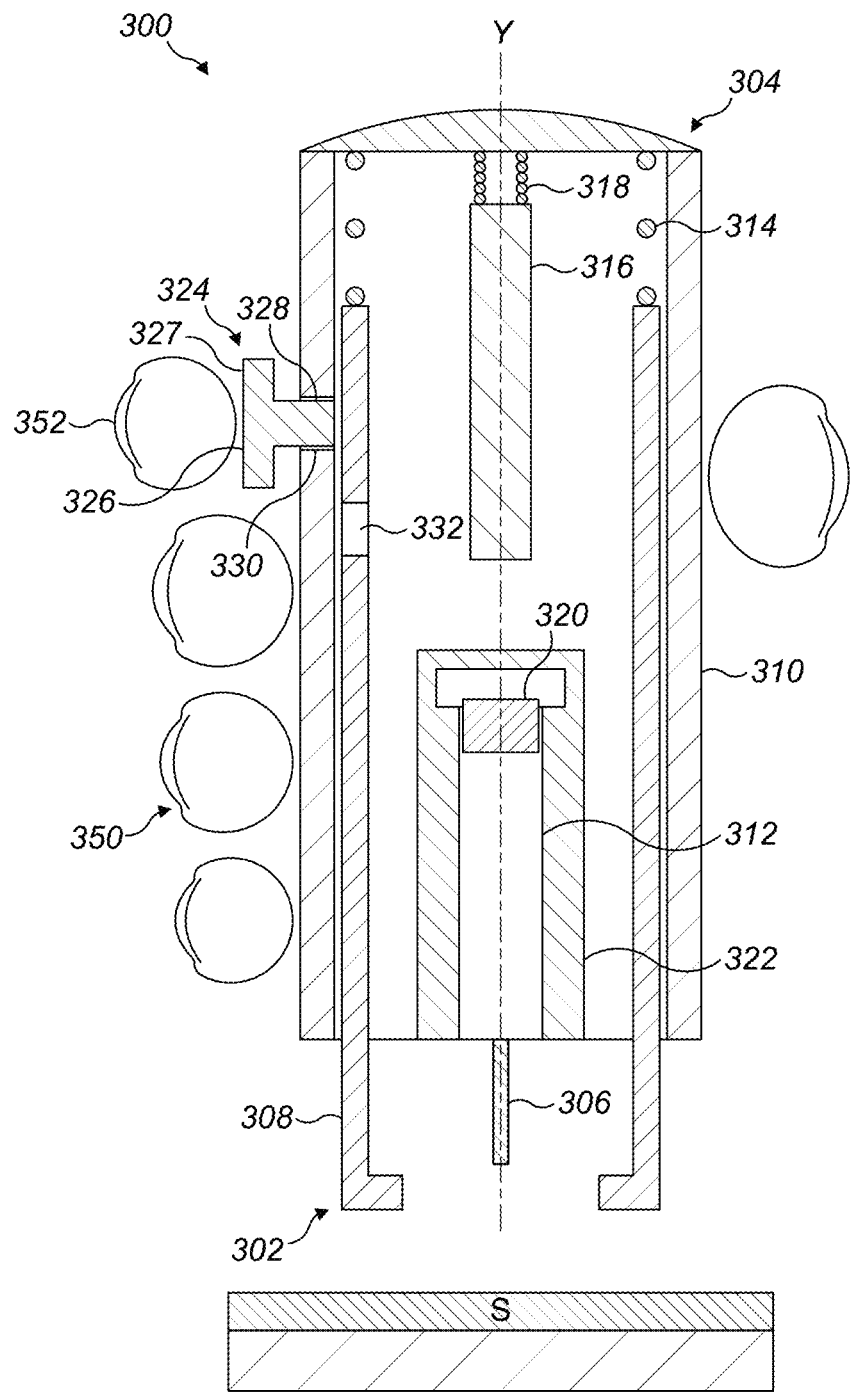
FIG. 3A shows a medicament delivery device according to a first embodiment n an initial state.
Figure 3B:
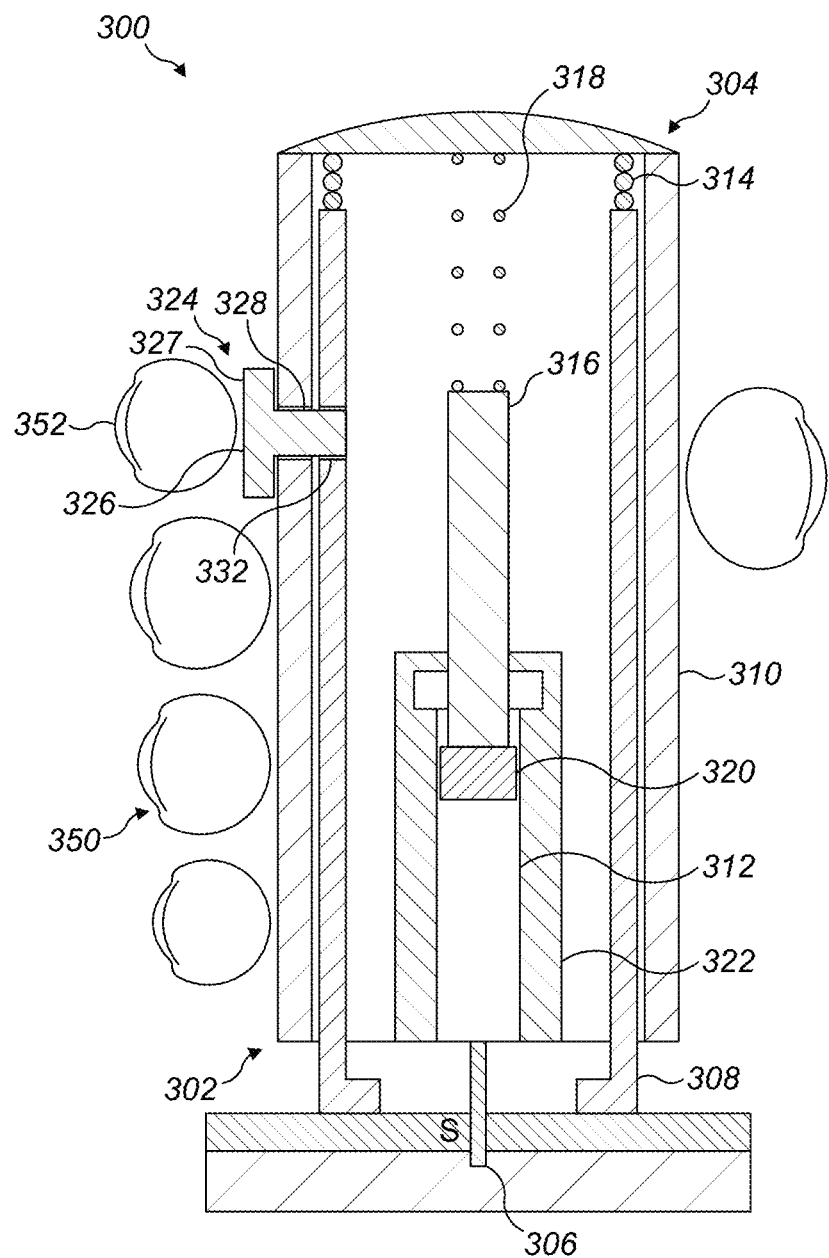
FIG. 3B shows the medicament delivery device of FIG. 3B in an activated state.

FIGS. 3A & 3B show features of a first embodiment of a medicament delivery device 300, which is also referred to herein as an injector device. These Figures show a cross section of the device 300 before and after activation of the device 300.

The device 300 has a distal end 302 and a proximal end 304 arranged along the longitudinal axis Y of the device 300. The device 300 has a needle 306 for injecting medicament into a user at an injection site S (such as the user's skin), a needle cover 308 and a body 310 (also known as a housing). The body 310 may be substantially cylindrical and has a substantially constant diameter along the longitudinal axis Y. The body 310 forms part of the external surface of the device 300 and is configured to be gripped by a user, as indicated by the user's hand 350 in FIGS. 3A and 3B.

The device 300 houses a pre-filled syringe 312 containing a medicament and a carrier 322 which supports the pre-filled syringe 312 within the body 310. The needle 306 is in fluid communication with the pre-filled syringe 312 and extends from the distal end of the pre-filled syringe 312. The needle cover 308 is axially movable relative to the body 310 between an initial, extended position, shown in FIG. 3A, in which the needle cover 308 covers (surrounds) the needle 306, and a retracted position, shown in FIG. 3B, for dispensing medicament from the device 300. In the retracted position, the needle 306 protrudes from the distal end of the needle cover 308.

A needle cover biasing member 314 such as a spring may be arranged in the body 310 to exert a biasing force against the needle cover 308 which biases the needle cover 308 axially, in the distal direction, from the retracted position towards the extended position. A force can be applied by the user against the biasing force of the needle cover biasing member 314 to move the needle cover 308 proximally from the extended position shown in FIG. 3A to the retracted position shown in FIG. 3B.

Medicament is dispensed from the medicament delivery device 300 via the needle 306 while the needle cover 308 is in the retracted position. An automated dispensing mechanism is triggered to start the dispensing of medicament when the needle cover 308 has moved proximally to reach a predetermined axial position within the body 310. The predetermined position may be located just distally of the retracted position, but in other cases may be located just proximally of the retracted position or may be the same as the retracted position.

The automated dispensing mechanism may comprise a plunger 316 that is automatically released when the needle cover 308 reaches the predetermined axial position. Once the plunger 316 is released, it moves distally within the pre-filled syringe 312 to dispense medicament from the pre-filled syringe 312 through the needle 306, in some embodiments by engaging a bung or piston 320 within the pre-filled syringe 312. The plunger 316 may be moved by a driving force provided by a plunger driving mechanism such as a drive spring 318, however other suitable forms of a plunger driving mechanism than a drive spring 318 may instead be used to move the plunger 316, such as an electromechanical motor or a gas cartridge.

In preparation for using the device 300 to administer the medicament, the user may remove a cap from the distal end 302 of the medicament delivery device 300. To initiate medicament delivery, the user presses the needle cover 308 against an injection site S such as the user's skin to move the needle cover 308 axially relative to the body 310 in a proximal direction and to uncover the needle 306. The needle 306 is pushed into the injection site S. The automated dispensing mechanism is released, and medicament is automatically dispensed from the device 300 via the needle 306. The user holds the needle cover 308 in the retracted position while the medicament is dispensed.

FIG. 3A shows the device 300 in a pre-use state, which may also be called an initial state or initial position. When the device 300 is in this state, the needle cover 308 is in an extended position with respect to the body 310 in which it covers the needle 306.

The device 300 comprises an actuation member 324 for holding the needle cover 308 in its retracted position. In the first embodiment, the actuation member 324 takes the form of a button arranged at an outer surface of the body 310. The actuation member 324 comprises an actuation element 326 arranged at an outer surface of the body 310 and having an actuation surface 327. The actuation member 324 further comprises a protrusion 328 disposed at the actuation element 326 and extending through an aperture 330 in the body 310. The actuation member 324 is movable with respect to the needle cover 308 between an initial position shown in FIG. 3A and an engaged position shown in FIG. 3B, as described below.

The needle cover 308 comprises a cooperating element 332, which may take the form of an aperture, a recess, a ridge or a frictional surface. The cooperating element 332 is arranged to be engaged by the protrusion 328 of the actuation member 324 when the needle cover 308 is in its retracted position and the actuation member 324 is in its engaged position, to hold the needle cover 308 in its retracted position.

FIG. 3A shows the actuation member 324 in its initial position with respect to the needle cover 308, in which the protrusion 328 is disengaged from the cooperating element 332, thereby allowing the needle cover 308 to axially move back and forth between its retracted position and its extended position. The device 300 may comprise a biasing member such as a spring that is configured to apply a biasing force to the actuation member 324 to bias the actuation member 324 into its initial position, from its engaged position.

As shown in FIG. 3A, when the needle cover 308 is in its extended position with respect to the body 310, the cooperating element 332 is not in alignment with the protrusion 328 of the actuation member 324. Due to this misalignment, the protrusion 328 cannot engage the cooperating element 332 to hold the needle cover 308 relative to the body 310 while the needle cover 308 is in its extended position. As shown in FIG. 3A, the actuation member 324 is prevented from being moved from its initial position to its engaged position to engage the cooperating element 332 due to an abutment between the protrusion 328 and an outer surface of the needle cover 308 while the needle cover 308 is in its extended position.

FIG. 3B shows the device 300 in an activated state. To transition the device 300 from the initial state shown in FIG. 3A to the activated state shown in FIG. 3B, a distal force is applied via the body 310 while the needle cover 308 is placed against the injection site S, such as the user's skin, causing the needle cover 308 to move proximally into the device 300.

When the device 300 is in the activated state as shown in FIG. 3B, the needle cover 308 is fully displaced into the device 300 and is in its retracted position. The needle 306 protrudes from the end of the needle cover 308 to its maximum extent. The medicament dispensing mechanism of the device 300 is triggered. In this example, triggering of the dispensing mechanism comprises the drive spring 318 being released such that it expands from a compressed state to an extended state, applying a distal force to a plunger 316 of the pre-filled syringe 312. The distal force causes the plunger 316 to move distally and in turn cause medicament to be expelled from the pre-filled syringe 312 via the needle 306.

The user should hold the device 300 steady against the injection site S while the medicament is being dispensed. During medicament delivery, the needle cover biasing member 314 continues to exert a biasing force against the needle cover 308 to bias the needle cover 308 axially, in the distal direction. Some users such as those with dexterity impairments may encounter difficulty in overcoming the biasing force to maintain the needle cover 308 in its retracted position while the medicament is being dispensed. Such users may find it difficult to hold the device 300 steady against the injection site S due to the strength of biasing force, causing them to move the device 300 before medicament delivery is complete. This could result in underdosing of medicament, leakage of medicament, and/or pain or discomfort for the user. The actuation member 324 of the device 300 may be used to overcome such issues by preventing the biasing force of the needle cover biasing member 314 from being transferred to the user when the actuation member 324 is in its engaged position.

The actuation member 324 is movable by the user from the initial position shown in FIG. 3A to an engaged position shown in FIG. 3B. To overcome the biasing force of the needle cover biasing member 314, the user can actuate the actuation member 324 while the needle cover 308 is in its retracted position such that the actuation member 324 moves from its initial position to its engaged position.

When the actuation member 324 is in its initial position, the protrusion 328 is disengaged from the cooperating element 332 and so the needle cover 308 can be axially moved between its retracted position and its extended position. However, when the actuation member 324 is in its engaged position (for example as shown in FIG. 3B), the actuation member 324 engages with the needle cover 308 to hold the needle cover 308 in its retracted position. More specifically, when the actuation member 324 is in its engaged position, the protrusion 328 of the actuation member 324 engages with the cooperating element 332 of the needle cover 308 to hold the needle cover 308 in its retracted position.

During proximal translation of the needle sleeve 308 from its extended position to its retracted position, the cooperating element 332 of the needle sleeve 308 is brought into (axial and radial) alignment with the protrusion 328 of the actuation member 324 such that, when the needle cover 308 is in its retracted position shown in FIG. 3B, the actuation member 324 is able to be moved from its initial position to its engaged position.

The actuation member 324 may be configured to be moved from its initial position to its engaged position by the user applying an actuation force to an outer surface of the actuation member 324, such as the actuation surface 327. As an example, the user may apply the actuation force by pushing the actuation surface 327 of the actuation member 324 with a finger 352 or thumb radially inwards, towards the needle cover 308. The user may apply the actuation force by making direct contact between their finger 352 and the actuation surface 327. The actuation force may be a separate force to any force provided by the user to retract the needle cover 308 and/or initiate medicament delivery. In other words, application of the actuation force may require a separate, distinct movement by the user to any movement used to retract the needle cover 308 and/or initiate medicament delivery.

Applying the actuation force to the actuation surface 327 causes the actuation element 326 and the protrusion 328 to move radially towards the needle cover 308, with the protrusion 328 translating through the aperture 330 in the body 310 to engage the cooperating element 332. Through the engagement between the protrusion 328 and the cooperating element 332, the needle cover 308 is held in the retracted position by the actuation member 324, as shown in FIG. 3B. More specifically, engagement between a distal-facing side of the cooperating element 332 and a proximal-facing side of the protrusion 328 (at the same time as engagement between a distal-facing side of the protrusion 328 and a proximal-facing side of the aperture 330) prevents distal movement of the needle cover 308 relative to the body 310. Proximal movement of the needle cover 308 relative to the body 310 may also be prevented by engagement between a proximal-facing side of the cooperating element 332 and a distal-facing side of the protrusion 328 (at the same time as engagement between a proximal-facing side of the protrusion 328 and a distal-facing side of the aperture 330).

Where the cooperating element 332 comprises an aperture or recess formed in the needle cover 308, the protrusion 328 may be dimensioned to have a slightly smaller cross-section than the aperture or recess. This is to allow for tolerance when inserting the protrusion 328 into the aperture or recess, but at the same time minimizing the amount of possible relative movement between the needle cover 308 and the body 310 while the actuation member 324 is in its engaged position that may occur if the cross-section of the aperture or recess is substantially greater than the cross-section of the protrusion 328.

The needle cover 308 is prevented from moving distally with respect to the body 310 while the actuation member 324 is in its engaged position, regardless of the biasing force exerted on the needle cover 308 by the needle cover biasing member 314. As a result, the biasing force exerted on the needle cover 308 is not transferred from the needle cover 308 to the injection site S. This means that the user is no longer required to overcome the biasing force of the needle cover biasing member 314 while the actuation member 324 is in its engaged position, making it easier for the user to hold the device 300 steady at the injection site S.

FIGS. 3A and 3B show the actuation member 324 located at the proximal end 304 of the device 300. Such a position may make it easier for the user to push the actuation member 324 using their index finger or thumb while they grasp the body 310 of the device 300 during a medicament delivery. However, it should be understood that the actuation member 324 may instead be located at a different region of the device 300 that is not at the proximal end 304.

After the medicament has been delivered, the user releases the actuation member 324 by removing their finger 352 from the actuation surface 327, thereby removing the actuation force applied to the actuation member 324. If the device 300 comprises a biasing member that is configured to bias the actuation member 324 from its engaged position to its initial position, the actuation member 324 may be caused to automatically return from its engaged position to its initial position once the actuation force is removed. Alternatively, if no biasing member is present then the user may manually move the actuation member 324 from its engaged position to its initial position.

In moving the actuation member 324 from its engaged position back to its initial position, the protrusion 328 moves radially away from the longitudinal axis Y of the device 300 and from the needle cover 308, disengaging the cooperating element 332 of the needle cover 308. As such, the needle cover 308 is no longer held in its retracted position by the actuation member 324 and is able to move distally with respect to the body 310. The user may then remove the device 300 from the injection site S. Since the needle cover 308 is no longer being held by the actuation member 324, the needle cover 308 moves distally from its retracted position to its initial position under the biasing force of the needle cover biasing member 314 once the body 310 and needle cover 308 are pulled away from the injection site S. The post-use state of the device 300 will appear similar to the pre-use state shown in FIG. 3A, where the needle cover 308 is in its initial position extending from the distal end 302 of the body 310 and covering the needle 306, however the plunger 316, drive spring 318 and piston 320 will each have moved distally.

The provision of a biasing member to bias the actuation member 324 towards its initial position can be beneficial in that it can ensure the actuation member 324 automatically returns to its initial position by default whenever it is not being actuated by a user, which in turn can ensure the needle cover 308 is automatically moved to its extended position to protect the user from the needle 306 by default. The presence of the biasing member may therefore improve the safety of the device 300 by reducing the likelihood of an accidental needle-stick event.

It has generally been described in relation to FIGS. 3A and 3B that, after the medicament has been delivered, the user releases the actuation member 324 before removing the device 300 from the injection site S. This order of steps can ensure that the needle cover 308 moves to cover the needle 306 as soon as the device 300 is removed from the injection site S, and therefore the needle 306 is not at any point exposed to the user (except when the distal end of the needle 306 is actually inserted into the user's skin during medicament delivery). However, it should be understood that in other instances the user may first remove the device 300 from the injection site 300 and subsequently release the actuation member 324.

FIGS. 4A to 4D show features of a second embodiment of a medicament delivery device 400, which is also referred to herein as an injector device. These Figures show a cross section of the device 400 before and after activation of the device 400. Certain features of the device 400 may be omitted from FIGS. 4A to 4D for clarity.

The device 400 has a distal end 402 and a proximal end 404 arranged along a longitudinal axis of the device 400. The device 400 has a needle 406 for injecting medicament into a user at an injection site (such as the user's skin), a needle cover 408 and a body 410 (also known as a housing). The body 410 may be substantially cylindrical and has a substantially constant diameter along the longitudinal axis. The body 410 forms part of the external surface of the device 400 and is configured to be gripped by a user during an injection process.

The device 400 houses a pre-filled syringe 412 containing a medicament and a carrier 422 which supports the pre-filled syringe 412 within the body 410. The needle 406 is in fluid communication with the pre-filled syringe 412 and extends from the distal end of the pre-filled syringe 412. The needle cover 408 is axially movable relative to the body 410 between an initial, extended position, shown in FIG. 4A, in which the needle cover 408 covers (surrounds) the needle 406, and a retracted position, shown in FIG. 4B, for dispensing medicament from the device 400. In the retracted position, the needle 406 protrudes from the distal end of the needle cover 408.

A needle cover biasing member such as a spring may be arranged in the body 410 (e.g. at a proximal end of the body 410) to exert a biasing force against the needle cover 408 which biases the needle cover 408 axially, in the distal direction. A force can be applied by the user against the biasing force of the needle cover biasing member to move the needle cover 408 proximally from the extended position shown in FIG. 4A to the retracted position shown in FIG. 4B.

Medicament is dispensed from the medicament delivery device 400 via the needle 406 while the needle cover 408 is in the retracted position. An automated dispensing mechanism is triggered to start the dispensing of medicament when the needle cover 408 has moved proximally to reach a predetermined axial position within the body 410. The predetermined position may be located just distally of the retracted position, but in other cases may be located just proximally of the retracted position or may be the same as the retracted position.

The automated dispensing mechanism may comprise a plunger that is automatically released when the needle cover 408 reaches the predetermined axial position. Once the plunger is released, it moves distally within the pre-filled syringe 412 to dispense medicament from the pre-filled syringe 412 through the needle 406. The plunger may be moved by a driving force provided by a plunger driving mechanism such as a drive spring, however other suitable forms of a plunger driving mechanism than a drive spring may instead be used to move the plunger, such as an electromechanical motor or a gas cartridge.

In preparation for using the device 400 to administer the medicament, the user may remove a cap from the distal end 402 of the medicament delivery device 400. To initiate medicament delivery, the user presses the needle cover 408 against an injection site such as the user's skin to move the needle cover 408 axially relative to the body 410 in a proximal direction and to uncover the needle 406. The needle 406 is pushed into the injection site. The automated dispensing mechanism is released, and medicament is automatically dispensed from the device 400 via the needle 406. The user holds the needle cover 408 in the retracted position while the medicament is dispensed.

Figure 4A:
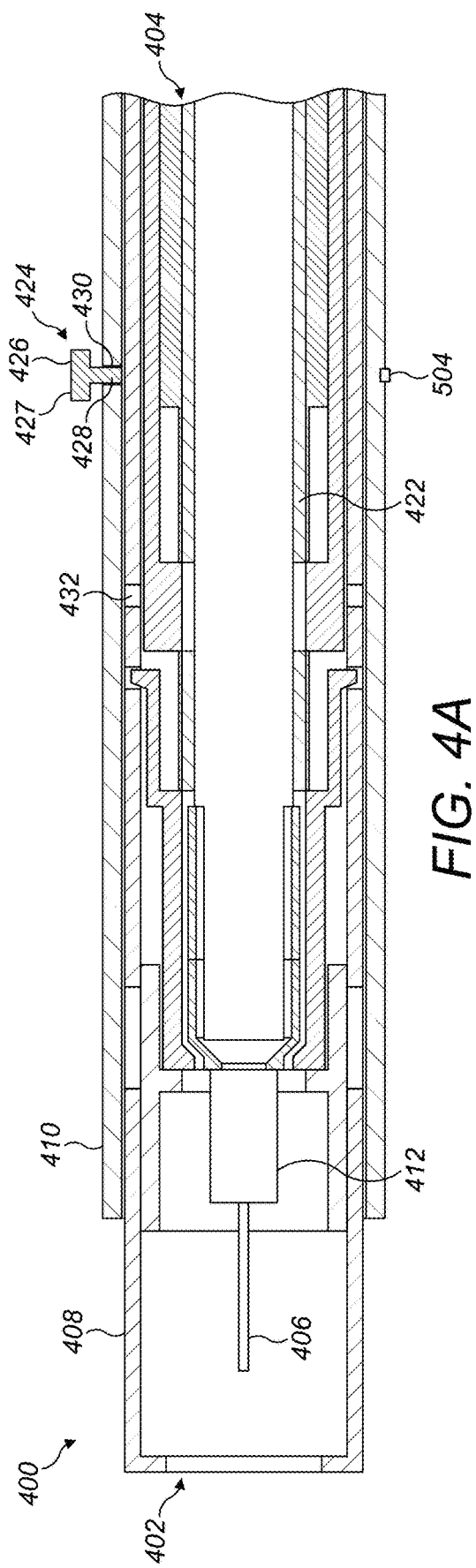
FIG. 4A shows a medicament delivery device according to a second embodiment in an initial state.

FIG. 4A shows the device 400 in a pre-use state, which may also be called an initial state or initial position. When the device 400 is in this state, the needle cover 408 is in an extended position with respect to the body 410 in which it covers the needle 406.

The device 400 comprises an actuation member 424 for holding the needle cover 408 in its retracted position. In the second embodiment, the actuation member 424 takes the form of a resilient collar arranged circumferentially around an outer surface of the body 410. The actuation member 424 comprises an actuation element 426 arranged at an outer surface of the body 410 and having an actuation surface 427. The actuation member 424 further comprises a protrusion 428 disposed at the actuation element 426 and extending through an aperture 430 in the body 410. The actuation member 424 is movable with respect to the needle cover 408 between an initial position shown in FIG. 4A and an engaged position shown in FIG. 4C, as described later.

Figure 5:
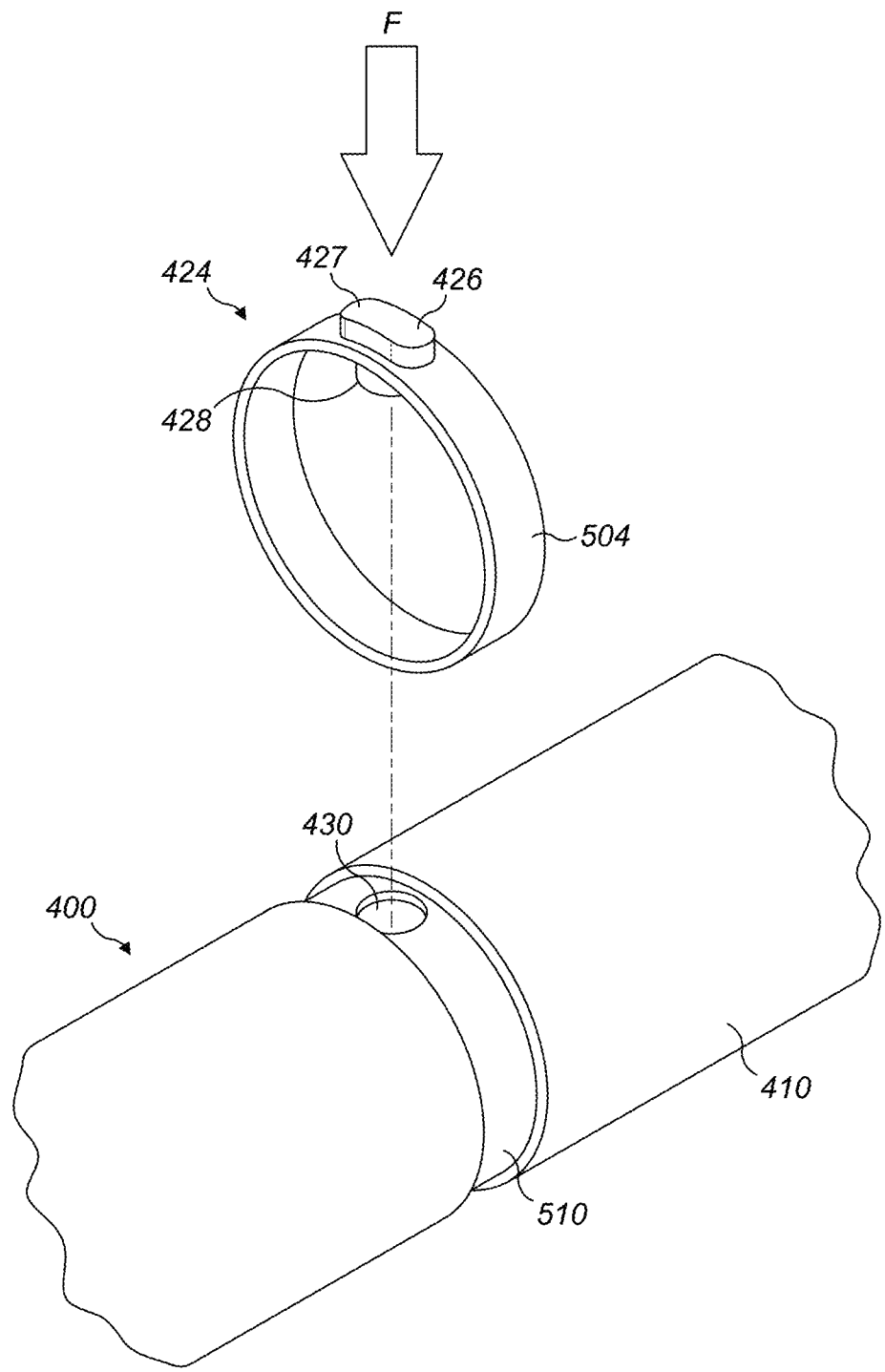
FIG. 5 shows is a perspective view of a portion of the medicament delivery device of the second embodiment.

Briefly turning to FIG. 5, an exploded perspective view of a portion of the device 400 of FIG. 4A is shown, showing the actuation member 424. In FIG. 5, the actuation member 424 is shown radially separated from the body 410 of the device 400 for the sake of more clearly showing the features of the actuation member 424. However, in actual use of the device 400, the actuation member 424 will be arranged circumferentially around an outer surface of the body 410. FIG. 5 shows the actuation element 426 of the actuation member 424 and the protrusion 428 extending away from the actuation element 426, radially towards the body 410 and the inside of the device 400. The protrusion 428 is aligned with the aperture 430 so that it may move through the aperture 430. A flexible portion 504 of the actuation member 424 is configured to surround the outer surface of the body 410 when the actuation member 424 is mounted on the body 410, to assist with holding the actuation member 424 in a fixed axial position along the body 410. The flexible portion may be configured to be received within a circumferential recess 510 formed in the outer surface of the body 410, to assist with holding the actuation member 424 in the fixed axial position along the body 410. The resilient nature of the flexible portion 504 allows the actuation member 424, and more particularly the flexible portion 504, to be deformed upon application of a force F to the actuation element 426 to move the actuation member 424 from its initial position to its engaged position, as described later.

Returning to FIG. 4A, the needle cover 408 comprises a cooperating element 432, which may take the form of an aperture, a recess, a ridge or a frictional surface. The cooperating element 432 is arranged to be engaged by the protrusion 428 of the actuation member 424 when the needle cover 408 is in its retracted position and the actuation member 424 is in its engaged position.

FIG. 4A shows the actuation member 424 in its initial position with respect to the needle cover 408, in which the protrusion 428 is disengaged from the cooperating element 432, thereby allowing the needle cover 408 to axially move back and forth between its retracted position and its extended position. The flexible portion 504 of the actuation member 424 acts a biasing member that is configured to apply a biasing force to the actuation member 424 to bias it into its initial position, from its engaged position.

As shown in FIG. 4A, when the needle cover 408 is in its extended position with respect to the body 410, the cooperating element 432 is not in alignment with the protrusion 428 of the actuation member 424. Due to this misalignment, the protrusion 428 cannot engage the cooperating element 432 to hold the needle cover 408 relative to the body 410 while the needle cover 408 is in its extended position. As shown in FIG. 4A, the actuation member 424 may be prevented from being moved from its initial position to its engaged position to engage the cooperating element 432 due to an abutment between the protrusion 428 and an outer surface of the needle cover 408 while the needle cover 408 is in its extended position.

Figure 4B:
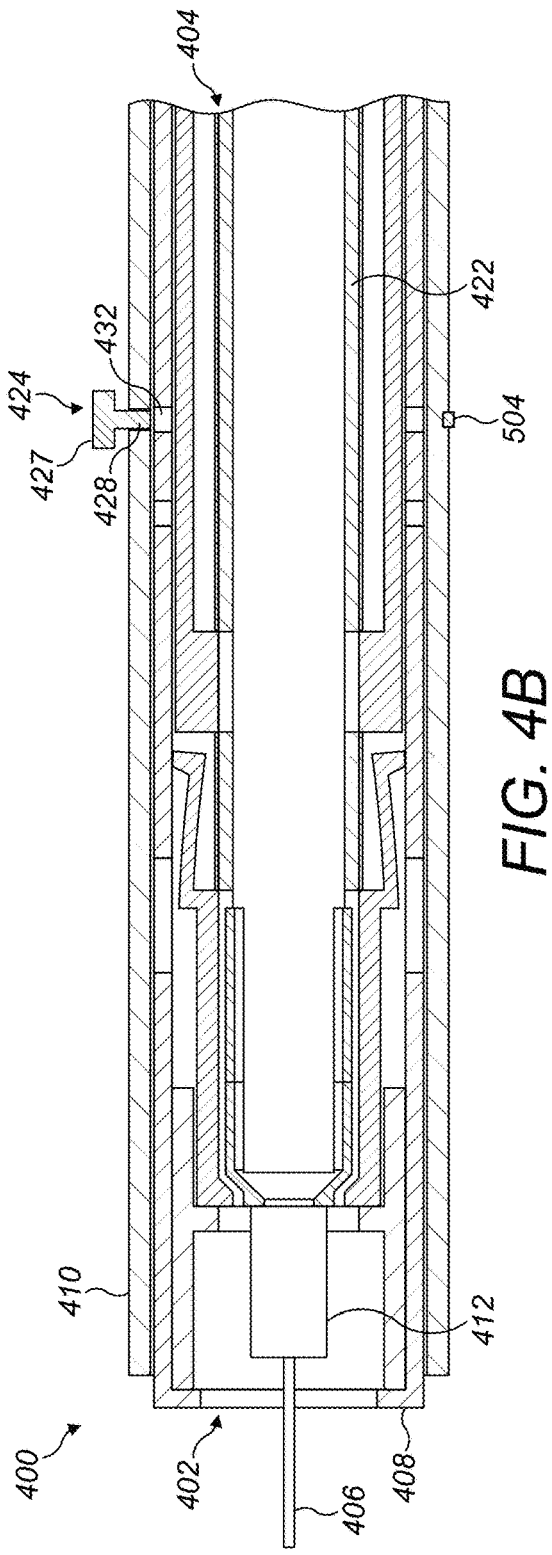
FIG. 4B shows the medicament delivery device of FIG. 4A in an activated state, with the actuation member in an initial position.

FIG. 4B shows the device 400 in an activated state. To transition the device 400 from the initial state shown in FIG. 4A to the activated state shown in FIG. 4B, a distal force is applied via the body 410 while the needle cover 408 is placed against the injection site, such as the user's skin, causing the needle cover 408 to move proximally into the device 400.

When the device 400 is in the activated state as shown in FIG. 4B, the needle cover 408 is fully displaced into the device 400 and is in its retracted position. The needle 406 protrudes from the end of the needle cover 408 to its maximum extent. The medicament dispensing mechanism of the device 400 is triggered. In this example, triggering of the dispensing mechanism comprises the drive spring being released such that the drive spring expands from a compressed state to an extended state, applying a distal force to a plunger of the pre-filled syringe 412. The distal force causes the plunger to move distally and in turn cause medicament to be expelled from the pre-filled syringe 412 via the needle 406.

The user should hold the device 400 steady against the injection site while the medicament is being dispensed. During medicament delivery, the needle cover biasing member continues to exert a biasing force against the needle cover 408 to bias the needle cover 408 axially, in the distal direction. The actuation member 424 of the device 400 may be used to overcome this biasing force.

The actuation member 424 is movable by the user from the initial position shown in FIG. 4B to an engaged position shown in FIG. 4C. To overcome the biasing force of the needle cover biasing member, the user can actuate the actuation member 424 while the needle cover 408 is in its retracted position such that the actuation member 424 moves from its initial position shown in FIG. 4B to its engaged position shown in FIG. 4C.

When the actuation member 424 is in its initial position (for example as shown in FIG. 4B), the protrusion 428 is disengaged from the cooperating element 432 and so the needle cover 408 can be axially moved between its retracted position and its extended position. However, when the actuation member 424 is in its engaged position (for example as shown in FIG. 4C), the actuation member 424 engages with the needle cover 408 to hold the needle cover 408 in its retracted position. More specifically, when the actuation member 424 is in its engaged position, the protrusion 428 of the actuation member 424 engages with the cooperating element 432 of the needle cover 408 to hold the needle cover 408 in its retracted position.

During proximal translation of the needle sleeve 408 from its extended position shown in FIG. 4A to its retracted position shown in FIG. 4B, the cooperating element 432 of the needle sleeve 408 is brought into (axial and radial) alignment with the protrusion 428 of the actuation member 424 such that, when the needle cover 408 is in its retracted position shown in FIG. 4B, the actuation member 424 is able to be moved from its initial position to its engaged position.

The actuation member 424 may be configured to be moved from its initial position to its engaged position by the user applying an actuation force F to an outer surface of the actuation member 424, such as the actuation surface 427. As an example, the user may apply the actuation force F by pushing the actuation surface 427 of the actuation member 424 with a finger or thumb radially inwards, towards the needle cover 408. The user may apply the actuation force F by making direct contact between their finger and the actuation surface 427. The actuation force F may be a separate force to any force provided by the user to retract the needle cover 408 and/or initiate medicament delivery. In other words, application of the actuation force F may require a separate, distinct movement by the user to any movement used to retract the needle cover 408 and/or initiate medicament delivery.

Applying the actuation force F to the actuation surface 427 causes the actuation element 426 and the protrusion 428 to move radially towards the needle cover 408, with the protrusion 428 translating through the aperture 430 in the body 410 to engage the cooperating element 432. Through the engagement between the protrusion 428 and the cooperating element 432, the needle cover 408 is held in the retracted position by the actuation member 424, as shown in FIG. 4C. More specifically, engagement between a distal-facing side of the cooperating element 432 and a proximal-facing side of the protrusion 428 (at the same time as engagement between a distal-facing side of the protrusion 428 and a proximal-facing side of the aperture 430) prevents distal movement of the needle cover 408 relative to the body 410. Proximal movement of the needle cover 408 relative to the body 410 may also be prevented by engagement between a proximal-facing side of the cooperating element 432 and a distal-facing side of the protrusion 428 (at the same time as engagement between a proximal-facing side of the protrusion 428 and a distal-facing side of the aperture 430).

Where the cooperating element 432 comprises an aperture or recess formed in the needle cover 408, the protrusion 428 may be dimensioned to have a slightly smaller cross-section than the aperture or recess, for similar reasons as previously described in relation to cooperating element 332 and protrusion 328.

The needle cover 408 is prevented from moving distally with respect to the body 410 while the actuation member 424 is in its engaged position, regardless of the biasing force exerted on the needle cover 408 by the needle cover biasing member. As a result, the biasing force exerted on the needle cover 408 by the needle cover biasing member is not transferred from the needle cover 408 to the injection site. This means that the user is no longer required to overcome the biasing force of the needle cover biasing member while the actuation member 424 is in its engaged position, making it easier for the user to hold the device 400 steady at the injection site.

After the medicament has been delivered, the user releases the actuation member 424 by removing their finger from the actuation surface 427 and thereby removing the actuation force F applied to the actuation member 424. As shown in FIG. 4D, the actuation member 424 may be caused to automatically return from its engaged position to its initial position once the actuation force F is removed, due to the flexible portion 504 acting as biasing member exerting a biasing force K to bias the actuation member 424 towards its initial position.

In moving the actuation member 424 from its engaged position back to its initial position, the protrusion 428 moves radially away from the longitudinal axis of the device 400 and from the needle cover 408, disengaging the cooperating element 432 of the needle cover 408, as shown in FIG. 4D. As such, the needle cover 408 is no longer held in its retracted position by the actuation member 424 and is able to move distally with respect to the body 410. The user may then remove the device 400 from the injection site. Since the needle cover 408 is no longer being held by the actuation member 424, the needle cover 408 moves distally from its retracted position to its initial position under the biasing force of the needle cover biasing member once the body 410 and needle cover 408 are pulled away from the injection site. The post-use state of the device 400 may appear similar to the pre-use state shown in FIG. 4A, where the needle cover 408 is in its initial position extending from the distal end 402 of the body 410 and covering the needle 406, however the plunger, drive spring and piston will each have been moved distally due to medicament delivery.

The provision of a biasing member to bias the actuation member 424 towards its initial position can be beneficial for similar reasons to those described in relation to FIGS. 3A & 3B and the biasing member used to bias the actuation member 324.

It has generally been described in relation to FIGS. 4A to 4D that, after the medicament has been delivered, the user releases the actuation member 424 before removing the device 400 from the injection site 400, however, it should be understood that in other instances the user may first remove the device 400 from the injection site and subsequently release the actuation member 424.

FIGS. 4A to 4D show the actuation member 424 located at the proximal end 404 of the device 400, however, it should be understood that the actuation member 424 may instead be located at a different region of the device 400 other than the proximal end 404.

FIGS. 6A to 6D show features of a third embodiment of a medicament delivery device 600, which is also referred to herein as an injector device. These Figures show a cross section of the device 600 before and after activation of the device 600. Certain features of the device 600 may be omitted from FIGS. 6A to 6D for clarity.

The device 600 has a distal end 602 and a proximal end 604 arranged along a longitudinal axis of the device 600. The device 600 has a needle 606 for injecting medicament into a user at an injection site (such as the user's skin), a needle cover 608 and a body 610 (also known as a housing). The body 610 may be substantially cylindrical and has a substantially constant diameter along the longitudinal axis. The body 610 forms part of the external surface of the device 600 and is configured to be gripped by a user during an injection process.

The device 600 houses a pre-filled syringe 612 containing a medicament and a carrier 622 which supports the pre-filled syringe 612 within the body 610. The needle 606 is in fluid communication with the pre-filled syringe 612 and extends from the distal end of the pre-filled syringe 612. The needle cover 608 is axially movable relative to the body 610 between an initial, extended position, shown in FIG. 6A, in which the needle cover 608 covers (surrounds) the needle 606, and a retracted position, shown in FIG. 6B, for dispensing medicament from the device 600. In the retracted position, the needle 606 protrudes from the distal end of the needle cover 608.

A needle cover biasing member such as a spring may be arranged in the body 610 to exert a biasing force against the needle cover 608 which biases the needle cover 608 axially, in the distal direction. A force can be applied by the user against the biasing force of the needle cover biasing member to move the needle cover 608 proximally from the extended position shown in FIG. 6A to the retracted position shown in FIG. 6B.

Medicament is dispensed from the medicament delivery device 600 via the needle 606 while the needle cover 608 is in the retracted position. An automated dispensing mechanism is triggered to start the dispensing of medicament when the needle cover 608 has moved proximally to reach a predetermined axial position within the body 610. The predetermined position may be located just distally of the retracted position, but in other cases may be located just proximally of the retracted position or may be the same as the retracted position.

The automated dispensing mechanism may comprise a plunger that is automatically released when the needle cover 608 reaches the predetermined axial position. Once the plunger is released, it moves distally within the pre-filled syringe 612 to dispense medicament from the pre-filled syringe 612 through the needle 606. The plunger may be moved by a driving force provided by a plunger driving mechanism such as a drive spring, however other suitable forms of a plunger driving mechanism than a drive spring may instead be used to move the plunger, such as an electromechanical motor or a gas cartridge.

In preparation for using the device 600 to administer the medicament, the user may remove a cap from the distal end 602 of the medicament delivery device 600. To initiate medicament delivery, the user presses the needle cover 608 against an injection site such as the user's skin to move the needle cover 608 axially relative to the body 610 in a proximal direction and to uncover the needle 606. The needle 606 is pushed into the injection site. The automated dispensing mechanism is released, and medicament is automatically dispensed from the device 600 via the needle 606. The user holds the needle cover 608 in the retracted position while the medicament is dispensed.

FIG. 6A shows the device 600 in a pre-use state, which may also be called an initial state or initial position. When the device 600 is in this state, the needle cover 608 is in an extended position with respect to the body 610 in which it covers the needle 606.

The device 600 comprises an actuation member 624 for holding the needle cover 608 in its retracted position. In the third embodiment, the actuation member 424 takes the form of a button arranged at an outer surface of the body 610. The actuation member 624 comprises an actuation element 626 arranged at an outer surface of the body 610 and having an actuation surface 627. The actuation member 624 further comprises a protrusion 628 disposed at the actuation element 626 and extending through an aperture 630 in the body 610. The actuation member 624 is movable with respect to the needle cover 608 between an initial position shown in FIG. 6A and an engaged position shown in FIG. 6C, as described later.

The needle cover 608 comprises a cooperating element 632, which may take the form of an aperture, a recess, a ridge or a frictional surface. The cooperating element 632 is arranged to be engaged by the protrusion 628 of the actuation member 624 when the needle cover 608 is in its retracted position and the actuation member 624 is in its engaged position.

FIG. 6A shows the actuation member 624 in an initial position with respect to the needle cover 608, in which the protrusion 628 is disengaged from the cooperating element 632, thereby allowing the needle cover 608 to axially move back and forth between its retracted position and its extended position. The device 600 comprises a biasing member 652 that is configured to bias the actuation member 624 into its initial position. As shown in FIG. 6A, the biasing member 652 comprises a leaf spring extending from the actuation element 626 to contact the outer surface of the body 610, however it should be understood that alternative forms of biasing member 652 may be used in different examples, for example a different type of spring, and/or that the biasing member 652 may be arranged in a different location. As shown in FIG. 6A, the actuation member 624 also comprises a stopping protrusion 650 extending from the protrusion 628 to retain the actuation member 624 in the body 610.

As shown in FIG. 6A, when the needle cover 608 is in its extended position with respect to the body 610, the cooperating element 632 is not in axial alignment with the protrusion 628. Due to this misalignment, the protrusion 628 cannot engage the cooperating element 632 to hold the needle cover 608 relative to the body 610 while the needle cover 608 is in its extended position. As shown in FIG. 6A, the actuation member 624 may be prevented from being moved from its initial position to its engaged position to engage the cooperating element 632 due to an abutment between the protrusion 628 and an outer surface of the needle cover 608 while the needle cover 608 is in its extended position.

FIG. 6B shows the device 600 in an activated state. To transition the device 600 from the initial state shown in FIG. 6A to the activated state shown in FIG. 6B, a distal force is applied via the body 610 while the needle cover 608 is placed against the injection site, such as the user's skin, causing the needle cover 608 to move proximally into the device 600.

When the device 600 is in the activated state as shown in FIG. 6B, the needle cover 608 is fully displaced into the device 600 and is in its retracted position. The needle 606 protrudes from the end of the needle cover 608 to its maximum extent. The medicament dispensing mechanism of the device 600 is triggered. In this example, triggering of the dispensing mechanism comprises the drive spring being released such that the drive spring expands from a compressed state to an extended state, applying a distal force to a plunger of the pre-filled syringe 612. The distal force causes the plunger to move distally and in turn cause medicament to be expelled from the pre-filled syringe 612 via the needle 606.

The actuation member 624 is movable by the user from the initial position shown in FIG. 6B to an engaged position shown in FIG. 6C. To overcome the biasing force of the needle cover biasing member, the user can actuate the actuation member 624 while the needle cover 608 is in its retracted position such that the actuation member 624 moves from its initial position shown in FIG. 6B to its engaged position shown in FIG. 6C.

When the actuation member 624 is in its initial position (for example as shown in FIG. 6B), the protrusion 628 is disengaged from the cooperating element 632 and so the needle cover 608 can be axially moved between its retracted position and its extended position. However, when the actuation member 624 is in its engaged position (for example as shown in FIG. 6C), the actuation member 624 engages with the needle cover 608 to hold the needle cover 608 in its retracted position. More specifically, when the actuation member 624 is in its engaged position, the protrusion 628 of the actuation member 624 engages with the cooperating element 632 of the needle cover 608 to hold the needle cover 608 in its retracted position.

During proximal translation of the needle sleeve 608 from its extended position shown in FIG. 6A to its retracted position shown in FIG. 6B, the cooperating element 632 of the needle sleeve 608 is brought into (axial and radial) alignment with the protrusion 628 of the actuation member 624 such that, when the needle cover 608 is in its retracted position shown in FIG. 6B, the actuation member 624 is able to be moved from its initial position to its engaged position.

The actuation member 624 may be configured to be moved from its initial position to its engaged position by the user applying an actuation force F to an outer surface of the actuation member 624, such as the actuation surface 627. As an example, the user may apply the actuation force F by pushing the actuation surface 627 of the actuation member 624 with a finger or thumb inwards, towards the needle cover 608. The user may apply the actuation force F by making direct contact between their finger and the actuation surface 627. The actuation force F may be a separate force to any force provided by the user to retract the needle cover 608 and/or initiate medicament delivery. In other words, application of the actuation force F may require a separate, distinct movement by the user to any movement used to retract the needle cover 608 and/or initiate medicament delivery.

Applying the actuation force F to the actuation surface 627 causes the actuation element 626 and the protrusion 628 to move radially towards the needle cover 608 against the biasing force of the biasing member 652, with the protrusion 628 translating through the aperture 630 in the body 610 to engage the cooperating element 632. Through the engagement between the protrusion 628 and the cooperating element 632, the needle cover 608 is held in the retracted position by the actuation member 624, as shown in FIG. 6C. More specifically, engagement between a distal-facing side of the cooperating element 632 and a proximal-facing side of the protrusion 628 (at the same time as engagement between a distal-facing side of the protrusion 628 and a proximal-facing side of the aperture 630) prevents distal movement of the needle cover 608 relative to the body 610.

Proximal movement of the needle cover 608 relative to the body 610 may also be prevented by engagement between a proximal-facing side of the cooperating element 632 and a distal-facing side of the protrusion 628 (at the same time as engagement between a proximal-facing side of the protrusion 628 and a distal-facing side of the aperture 630).

Where the cooperating element 632 comprises an aperture or recess formed in the needle cover 608, the protrusion 628 may be dimensioned to have a slightly smaller cross-section than the aperture or recess, for similar reasons as previously described in relation to cooperating element 332 and protrusion 328.

The needle cover 608 is prevented from moving distally with respect to the body 610 while the actuation member 624 is in its engaged position, regardless of the biasing force exerted on the needle cover 608 by the needle cover biasing member 614. As a result, the biasing force exerted on the needle cover 608 by the needle cover biasing member is not transferred from the needle cover 608 to the injection site. This means that the user is no longer required to overcome the biasing force of the needle cover biasing member while the actuation member 624 is in its engaged position, making it easier for the user to hold the device 600 steady at the injection site.

After the medicament has been delivered, the user releases the actuation member 624 by removing their finger from the actuation surface 627 and thereby removing the actuation force F applied to the actuation member 624. As shown in FIG. 6D, the actuation member 624 is caused to automatically return from its engaged position to its initial position once the actuation force F is removed, due to the biasing member 652 exerting a biasing force K to bias the actuation member 624 towards its initial position.

In moving the actuation member 624 from its engaged position back to its initial position, the protrusion 628 moves radially away from the longitudinal axis of the device 600 and from the needle cover 608, disengaging the cooperating element 632 of the needle cover 608, as shown in FIG. 6D. As such, the needle cover 608 is no longer held in its retracted position by the actuation member 624 and is able to move distally with respect to the body 610. The user may then remove the device 600 from the injection site. Since the needle cover 608 is no longer being held by the actuation member 624, the needle cover 608 moves distally from its retracted position to its initial position under the biasing force of the needle cover biasing member once the body 610 and needle cover 608 are pulled away from the injection site. The post-use state of the device 600 may appear similar to the pre-use state shown in FIG. 6A, where the needle cover 608 is in its initial position extending from the distal end 602 of the body 610 and covering the needle 606, however the plunger, drive spring and piston will each have been moved distally due to medicament delivery.

The provision of a biasing member 652 to bias the actuation member 624 towards its initial position can be beneficial for similar reasons to those described in relation to FIGS. 3A & 3B.

It has generally been described in relation to FIGS. 6A to 6D that, after the medicament has been delivered, the user releases the actuation member 624 before removing the device 600 from the injection site 600, however, it should be understood that in other instances the user may first remove the device 600 from the injection site and subsequently release the actuation member 624.

FIGS. 6A to 6D show the actuation member 624 located at the proximal end 604 of the device 600, however, it should be understood that the actuation member 624 may instead be located at a different region of the device 600 that is not at the proximal end 604.

FIGS. 7A to 7D show features of a fourth embodiment of a medicament delivery device 700, which is also referred to herein as an injector device. These Figures show a cross section of the device 700 before and after activation of the device 700. Certain features of the device 700 may be omitted from FIGS. 7A to 7D for clarity.

The device 700 has a distal end 702 and a proximal end 704 arranged along a longitudinal axis of the device 700. The furthest proximal end of the device 700 is omitted from FIGS. 7A to 7D for clarity. The device 700 has a needle 706 for injecting medicament into a user at an injection site (such as the user's skin), a needle cover 708 and a body 710 (also known as a housing). The body 710 may be substantially cylindrical and has a substantially constant diameter along the longitudinal axis. The body 710 forms part of the external surface of the device 700 and is configured to be gripped by a user during an injection process.

The device 700 houses a pre-filled syringe 712 containing a medicament and a carrier 722 which supports the pre-filled syringe 712 within the body 710. The needle 706 is in fluid communication with the pre-filled syringe 712 and extends from the distal end of the pre-filled syringe 712. The needle cover 708 is axially movable relative to the body 710 between an initial, extended position, shown in FIG. 7A, in which the needle cover 708 covers (surrounds) the needle 706, and a retracted position, shown in FIG. 7B, for dispensing medicament from the device 700. In the retracted position, the needle 706 protrudes from the distal end of the needle cover 708.

A needle cover biasing member such as a spring may be arranged in the body 710 to exert a biasing force against the needle cover 708 which biases the needle cover 708 axially, in the distal direction. A force can be applied by the user against the biasing force of the needle cover biasing member to move the needle cover 708 proximally from the extended position shown in FIG. 7A to the retracted position shown in FIG. 7B.

Medicament is dispensed from the medicament delivery device 700 via the needle 706 while the needle cover 708 is in the retracted position. An automated dispensing mechanism is triggered to start the dispensing of medicament when the needle cover 708 has moved proximally to reach a predetermined axial position within the body 710. The predetermined position may be located just distally of the retracted position, but in other cases may be located just proximally of the retracted position or may be the same as the retracted position.

The automated dispensing mechanism may comprise a plunger that is automatically released when the needle cover 708 reaches the predetermined axial position. Once the plunger is released, it moves distally within the pre-filled syringe 712 to dispense medicament from the pre-filled syringe 712 through the needle 706. The plunger may be moved by a driving force provided by a plunger driving mechanism such as a drive spring, however other suitable forms of a plunger driving mechanism than a drive spring may instead be used to move the plunger, such as an electromechanical motor or a gas cartridge.

In preparation for using the device 700 to administer the medicament, the user may remove a cap from the distal end 702 of the medicament delivery device 700. To initiate medicament delivery, the user presses the needle cover 708 against an injection site such as the user's skin to move the needle cover 708 axially relative to the body 710 in a proximal direction and to uncover the needle 706. The needle 706 is pushed into the injection site. The automated dispensing mechanism is released, and medicament is automatically dispensed from the device 700 via the needle 706. The user holds the needle cover 708 in the retracted position while the medicament is dispensed.

FIG. 7A shows the device 700 in a pre-use state, which may also be called an initial state or initial position. When the device 700 is in this state, the needle cover 708 is in an extended position with respect to the body 710 in which it covers the needle 706.

The device 700 comprises an actuation member 724 for holding the needle cover 708 in its retracted position. In the fourth embodiment, the actuation member 724 takes the form of a button integrally formed with the body 710. The actuation member 724 comprises an actuation element 726 having an actuation surface 727, and one or more flexible portions 750a, 750b resiliently coupling the actuation element 726 to the remainder of the body 710. The actuation member 724 further comprises a protrusion 728 disposed at a rear surface of the actuation element 726 and extending radially towards the needle cover 708. The actuation member 724 is movable with respect to the needle cover 708 between an initial position shown in FIG. 7A and an engaged position shown in FIG. 7C, as described later.

The needle cover 708 comprises a cooperating element 732, which may take the form of an aperture, a recess, a ridge or a frictional surface. The cooperating element 732 is arranged to be engaged by the protrusion 728 of the actuation member 724 when the needle cover 708 is in its retracted position and the actuation member 724 is in its engaged position.

FIG. 7A shows the actuation member 724 in its initial position in which the protrusion 728 is disengaged from the cooperating element 732, thereby allowing the needle cover 708 to axially move back and forth between its retracted position and its extended position. The one or more flexible portions 750a, 750b act as a biasing member to bias the actuation member 724 into its initial position, from its engaged position.

As shown in FIG. 7A, when the needle cover 708 is in its extended position with respect to the body 710, the cooperating element 732 is not in alignment with the protrusion 728. Due to this misalignment, the protrusion 728 cannot engage the cooperating element 732 to hold the needle cover 708 relative to the body 710 while the needle cover 708 is in its extended position. As shown in FIG. 7A, the actuation member 724 may be prevented from being moved from its initial position to its engaged position to engage the cooperating element 732 due to an abutment between the protrusion 728 and an outer surface of the needle cover 708 while the needle cover 708 is in its extended position.

FIG. 7B shows the device 700 in an activated state. To transition the device 700 from the initial state shown in FIG. 7A to the activated state shown in FIG. 7B, a distal force is applied via the body 710 while the needle cover 708 is placed against the injection site, such as the user's skin, causing the needle cover 708 to move proximally into the device 700.

When the device 700 is in the activated state as shown in FIG. 7B, the needle cover 708 is fully displaced into the device 700 and is in its retracted position. The needle 706 protrudes from the end of the needle cover 708 to its maximum extent. The medicament dispensing mechanism of the device 700 is triggered. In this example, triggering of the dispensing mechanism comprises the drive spring being released such that the drive spring expands from a compressed state to an extended state, applying a distal force to a plunger of the pre-filled syringe 712. The distal force causes the plunger to move distally and in turn cause medicament to be expelled from the pre-filled syringe 712 via the needle 706.

The actuation member 724 is movable by the user from the initial position shown in FIG. 7B to an engaged position shown in FIG. 7C. To overcome the biasing force of the needle cover biasing member, the user can actuate the actuation member 724 while the needle cover 708 is in its retracted position such that the actuation member 724 moves from its initial position shown in FIG. 7B to its engaged position shown in FIG. 7C.

When the actuation member 724 is in its initial position (for example as shown in FIG. 7B), the protrusion 728 is disengaged from the cooperating element 732 and so the needle cover 708 can be axially moved between its retracted position and its extended position. However, when the actuation member 724 is in its engaged position (for example as shown in FIG. 7C), the actuation member 724 engages with the needle cover 708 to hold the needle cover 708 in its retracted position. More specifically, when the actuation member 724 is in its engaged position, the protrusion 728 of the actuation member 724 engages with the cooperating element 732 of the needle cover 708 to hold the needle cover 708 in its retracted position.

During proximal translation of the needle sleeve 708 from its extended position shown in FIG. 7A to its retracted position shown in FIG. 7B, the cooperating element 732 of the needle sleeve 708 is brought into (axial and radial) alignment with the protrusion 728 of the actuation member 724 such that, when the needle cover 708 is in its retracted position shown in FIG. 7B, the actuation member 724 is able to be moved from its initial position to its engaged position.

The actuation member 724 may be configured to be moved from its initial position to its engaged position by the user applying an actuation force F to an outer surface of the actuation member 724, such as the actuation surface 727. As an example, the user may apply the actuation force F by pushing the actuation surface 727 of the actuation member 724 with a finger or thumb radially inwards, towards the needle cover 708. The user may apply the actuation force F by making direct contact between their finger and the actuation surface 727. The actuation force F may be a separate force to any force provided by the user to retract the needle cover 708 and/or initiate medicament delivery. In other words, application of the actuation force F may require a separate, distinct movement by the user to any movement used to retract the needle cover 708 and/or initiate medicament delivery.

Applying the actuation force F to the actuation surface 727 causes the actuation element 726 and the protrusion 728 to move radially towards the needle cover 408 against the biasing force of the one or more flexible portions 750a, 750b such that the protrusion 728 engages the cooperating element 732. Through the engagement between the protrusion 728 and the cooperating element 732, the needle cover 708 is held in the retracted position by the actuation member 724, as shown in FIG. 7C. More specifically, engagement between a distal-facing side of the cooperating element 732 and a proximal-facing side of the protrusion 728 (with the protrusion 728 being axially fixed relative to the body 710 by the one or more flexible portions 750a, 750b) prevents distal movement of the needle cover 708 relative to the body 710. Proximal movement of the needle cover 708 relative to the body 710 may also be prevented by engagement between a proximal-facing side of the cooperating element 732 and a distal-facing side of the protrusion 728.

Where the cooperating element 732 comprises an aperture or recess formed in the needle cover 708, the protrusion 728 may be dimensioned to have a slightly smaller cross-section than the aperture or recess, for similar reasons as previously described in relation to cooperating element 332 and protrusion 328.

The needle cover 708 is prevented from moving distally with respect to the body 710 while the actuation member 724 is in its engaged position, regardless of the biasing force exerted on the needle cover 708 by the needle cover biasing member 714. As a result, the biasing force exerted on the needle cover 708 by the needle cover biasing member is not transferred from the needle cover 708 to the injection site. This means that the user is no longer required to overcome the biasing force of the needle cover biasing member while the actuation member 724 is in its engaged position, making it easier for the user to hold the device 700 steady at the injection site.

After the medicament has been delivered, the user releases the actuation member 724 by removing their finger from the actuation surface 727 and thereby removing the actuation force F applied to the actuation member 724. As shown in FIG. 7D, the actuation member 724 is caused to automatically return from its engaged position to its initial position once the actuation force F is removed, due to the one or more flexible portions 750a, 750b acting a biasing member and exerting a biasing force K to bias the actuation member 724 towards its initial position.

In moving the actuation member 724 from its engaged position back to its initial position, the protrusion 728 moves radially away from the longitudinal axis of the device 700 and from the needle cover 708, disengaging the cooperating element 732 of the needle cover 708, as shown in FIG. 7D. As such, the needle cover 708 is no longer held in its retracted position by the actuation member 724 and is able to move distally with respect to the body 710. The user may then remove the device 700 from the injection site. Since the needle cover 708 is no longer being held by the actuation member 724, the needle cover 708 moves distally from its retracted position to its initial position under the biasing force of the needle cover biasing member once the body 710 and needle cover 708 are pulled away from the injection site. The post-use state of the device 700 may appear similar to the pre-use state shown in FIG. 7A, where the needle cover 708 is in its initial position extending from the distal end 702 of the body 710 and covering the needle 706, however the plunger, drive spring and piston will each have been moved distally due to medicament delivery.

The provision of one or more flexible portions 750a, 750b acting as a biasing member to bias the actuation member 724 towards its initial position can be beneficial for similar reasons to those described in relation to FIGS. 3A & 3B and the biasing member used to bias the actuation member 324.

It has generally been described in relation to FIGS. 7A to 7D that, after the medicament has been delivered, the user releases the actuation member 724 before removing the device 700 from the injection site, however, it should be understood that in other instances the user may first remove the device 700 from the injection site and subsequently release the actuation member 724.

FIGS. 7A to 7D show the actuation member 724 located at the proximal end 704 of the device 700, however, it should be understood that the actuation member 724 may instead be located at a different region of the device 700 that is not at the proximal end 704.

FIGS. 8A to 8D show features of a fifth embodiment of a medicament delivery device 800, which is also referred to herein as an injector device. These Figures each show a cross section of the device 800 during various stages of activation of the device 800. Certain features of the device 800 may have been omitted from FIGS. 8A to 8D for clarity.

The device 800 may have a similar form as a medicament delivery device described previously, having a distal end 802 and a proximal end 804 arranged along a longitudinal axis of the device 800. The device 800 has a needle for injecting medicament into a user at an injection site (such as the user's skin), a needle cover 808 and a body 810 (also known as a housing). The body 810 may be substantially cylindrical and has a substantially constant diameter along the longitudinal axis. The body 810 forms part of the external surface of the device 800 and is configured to be gripped by a user during an injection process.

The device 800 houses a pre-filled syringe 812 containing a medicament and a carrier 822 which supports the pre-filled syringe 812 within the body 810. The needle is in fluid communication with the pre-filled syringe 812 and extends from the distal end of the pre-filled syringe 812. The needle cover 808 is axially movable relative to the body 810 between an initial, extended position, shown in FIG. 8A, in which the needle cover 808 covers (surrounds) the needle, and a retracted position, shown in FIG. 8B, for dispensing medicament from the device 800. In the retracted position, the needle protrudes from the distal end of the needle cover 808.

A needle cover biasing member 896 such as a spring may be arranged in the body 810 (e.g. at a proximal end of the body 810) to exert a biasing force against the needle cover 808 which biases the needle cover 808 axially, in the distal direction. The needle cover biasing member 896 may exert the biasing force against the needle cover 808 via a collar 870 arranged concentrically about the longitudinal axis of the device 800, where the collar 870 is configured to move axially within the device 800 to transfer the biasing force from the needle cover biasing member 896 to the needle cover 808. However, in other examples the collar 870 may not be present and the needle cover biasing member 896 may act directly on the needle cover 808.

Medicament is dispensed from the medicament delivery device 800 via the needle while the needle cover 808 is in the retracted position. An automated dispensing mechanism is triggered to start the dispensing of medicament when the needle cover 808 has moved proximally to reach a predetermined axial position within the body 810. The predetermined position may be located just distally of the retracted position, but in other cases may be located just proximally of the retracted position or may be the same as the retracted position.

The automated dispensing mechanism may comprise a plunger 894 that is automatically released when the needle cover 808 reaches the predetermined axial position. Once the plunger 816 is released, it moves distally within the pre-filled syringe 812 to dispense medicament from the pre-filled syringe 812 through the needle. The plunger 894 may be moved by a driving force provided by a plunger driving mechanism such as a drive spring 898, however other suitable forms of a plunger driving mechanism than a drive spring 898 may instead be used to move the plunger 894, such as an electromechanical motor or a gas cartridge.

In preparation for using the device 800 to administer the medicament, the user may remove a cap from the distal end 802 of the medicament delivery device 800. To initiate medicament delivery, the user presses the needle cover 808 against an injection site such as the user's skin to move the needle cover 808 axially relative to the body 810 in a proximal direction and to uncover the needle. The needle is pushed into the injection site. The automated dispensing mechanism is released, and medicament is automatically dispensed from the device 800 via the needle. The user holds the needle cover 808 in the retracted position while the medicament is dispensed.

Figure 8A:
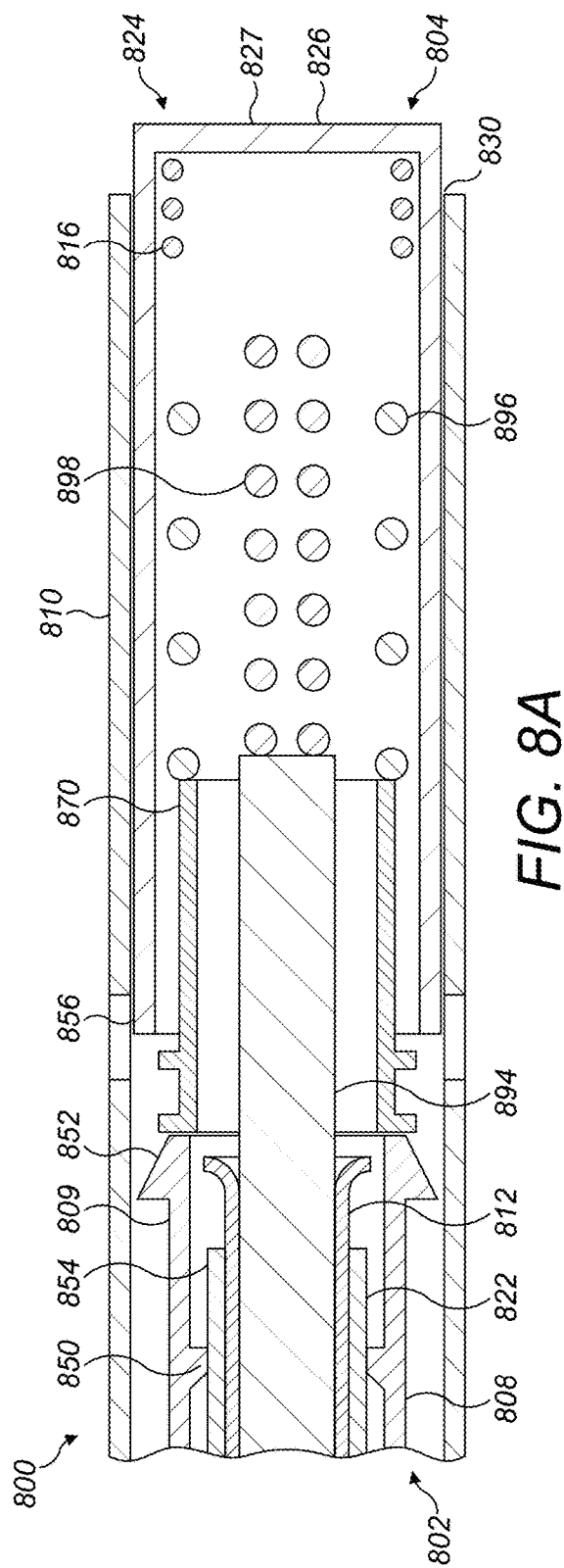
FIG. 8A shows a medicament delivery device according to a fifth embodiment in an initial state.

FIG. 8A shows the device 800 in a pre-use state, which may also be called an initial state or initial position. When the device 800 is in this state, the needle cover 808 is in an extended position with respect to the body 810 in which it covers the needle.

The device 800 comprises an actuation member 824 for holding the needle cover 808 in its retracted position. In the fifth embodiment, the actuation member 824 takes the form of a button arranged to extend through an opening 830 at a proximal end face of the body 810. The actuation member 824 comprises an actuation element 826 having a proximally-facing actuation surface 827, and one or more elongate arms 856 extending distally from a distal-facing surface of the actuation element 826. The one or more elongate arms 856 extend distally within the body 810.

The needle cover 808 comprises a resilient member 809 at a proximal end thereof for engaging with a cooperating element 854 of the medicament delivery device 800. The resilient member 809 may take the form of a flexible arm extending proximally and having a first protrusion 850 and a second protrusion 852 each disposed at a free end of the flexible arm, in opposite directions. The first protrusion 850 may extend from the flexible arm towards the carrier 822, while the second protrusion 852 may extend away from the carrier 822 and toward the body 810.

The actuation member 824, when moved from an initial position to an engaged position, is configured to cause the resilient member 809 to be deflected (as indicated by pivot arrow 890*a*) such that the resilient member 809 engages the cooperating element 854, to hold the needle cover 808 in its retracted position. More particularly, the actuation member 824, when moved from the initial position to the engaged position, is configured to cause flexible arm of the resilient member 809 to be deflected such that the first protrusion 850 engages the cooperating element 854, to hold the needle cover 808 in its retracted position.

The cooperating element 854 may take the form of an aperture, a recess, a ridge, or a frictional surface. FIG. 8A shows the cooperating element 854 formed at the carrier 822, the cooperating element 854 comprising a proximal-facing edge of the carrier 822.

FIG. 8A shows the actuation member 824 in an initial position. The actuation member 824 may be biased into the initial position by a biasing member 816 such as a spring. While the actuation member 824 is in its initial position, the resilient member 809 is disengaged from the cooperating element 854, thereby allowing the needle cover 808 to axially move back and forth between its retracted position and its extended position. More specifically, while the actuation member 824 is in its initial position, the first protrusion 850 of the flexible arm is disengaged from the cooperating element 854 formed at the carrier 822, thereby allowing the needle cover 808 to axially move back and forth between its retracted position and its extended position.

As shown in FIG. 8A, when the needle cover 808 is in its extended position with respect to the body 810, the first protrusion 850 of the resilient member 809 is not in alignment with the cooperating element 854. Due to this misalignment, the first protrusion 850 does not hold the needle cover 808 relative to the body 810 while the needle cover 808 is in its extended position. As shown in FIG. 8A, the first protrusion 850 is located against an outer surface of the carrier 822 while the needle cover 808 is in its extended position.

Figure 8B:
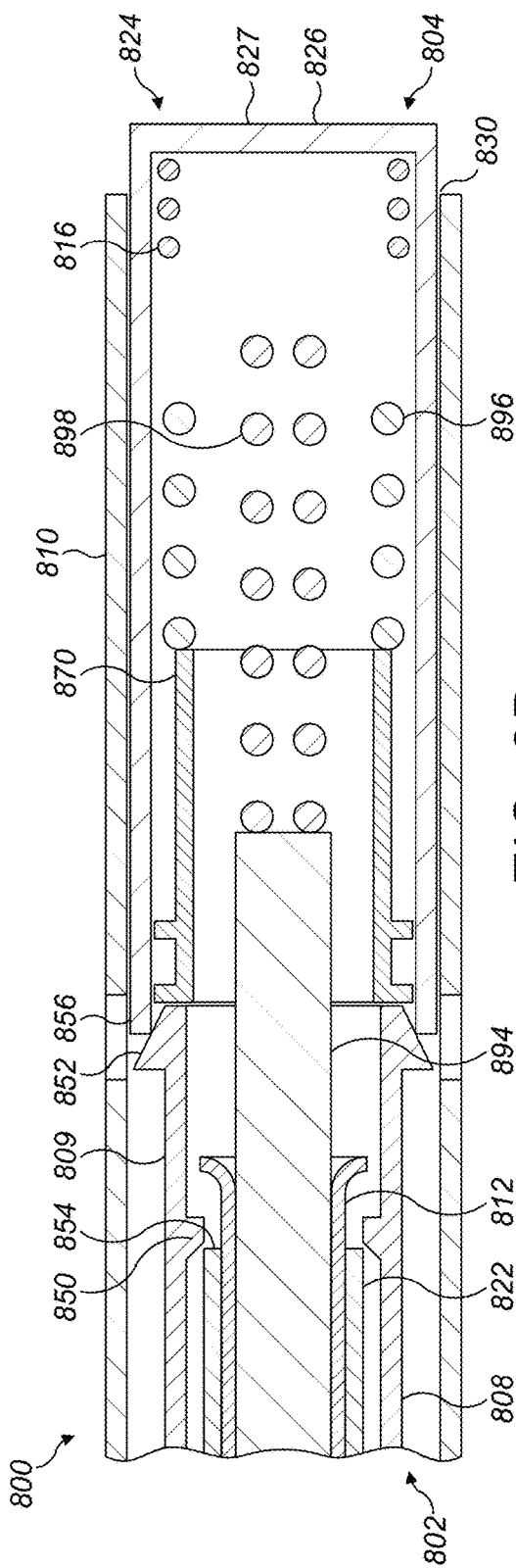
FIG. 8B shows the medicament delivery device of FIG. 8A in an activated state, with the actuation member in an initial position.

FIG. 8B shows the device 800 in an activated state. To transition the device 800 from the initial state shown in FIG. 8A to the activated state shown in FIG. 8B, a distal force is applied via the body 810 while the needle cover 808 is placed against the injection site, such as the user's skin, causing the needle cover 808 to move proximally into the device 800 against the biasing force of the needle cover biasing member 896.

When the device 800 is in the activated state as shown in FIG. 8B, the needle cover 808 is fully displaced into the device 800 and is in its retracted position. The needle protrudes from the end of the needle cover 808 to its maximum extent. The medicament dispensing mechanism of the device 800 is triggered. In this example, triggering of the dispensing mechanism comprises the drive spring 898 being released such that the drive spring 898 expands from a compressed state to an extended state, applying a distal force to a plunger 894 of the pre-filled syringe 812. The distal force causes the plunger 894 to move distally and in turn cause medicament to be expelled from the pre-filled syringe 812 via the needle.

Figure 8C:
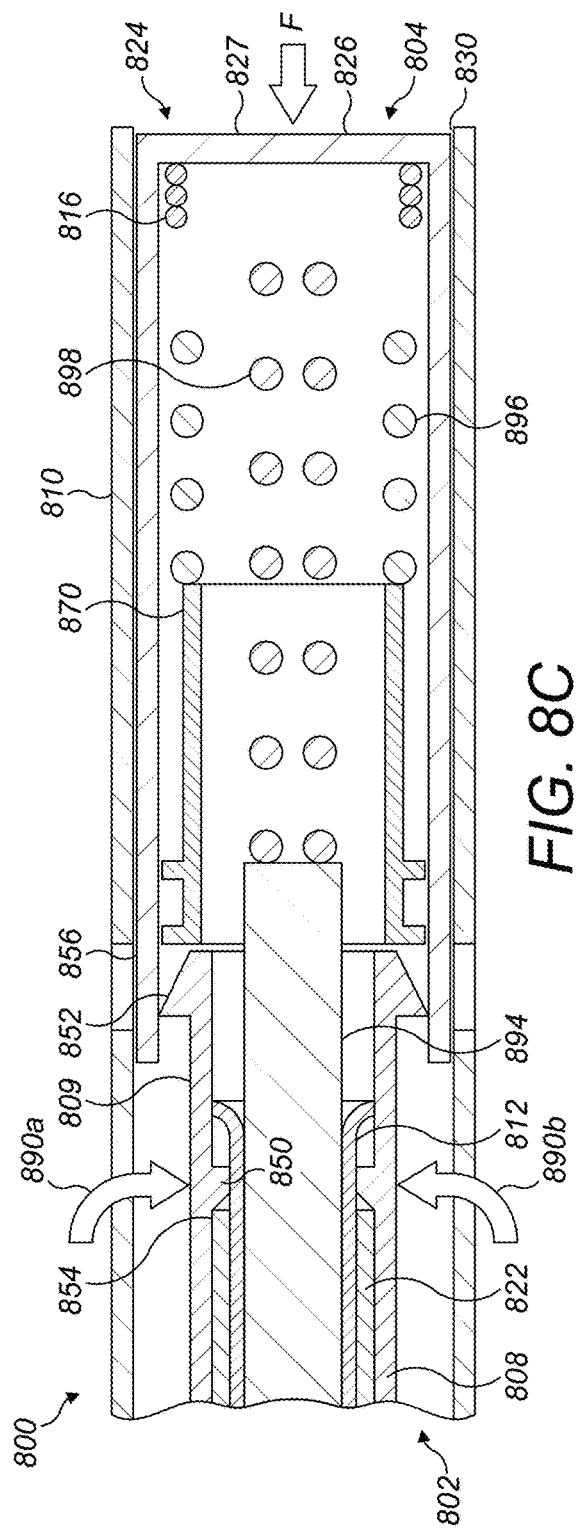
FIG. 8C shows the medicament delivery device of FIG. 8B with the actuation member in an engaged position.

To overcome the biasing force of the needle cover biasing member 896, the user can actuate the actuation member 824 while the needle cover 808 is in its retracted position such that the actuation member 824 moves distally from its initial position shown in FIG. 8B to its engaged position shown in FIG. 8C.

When the actuation member 824 is in its initial position (for example as shown in FIG. 8B), the elongate arm 856 does not deflect the flexible arm. As such, the first protrusion 850 remains disengaged from the cooperating element 854 and so the needle cover 808 can be axially moved between its retracted position and its extended position. However, when the actuation member 824 is moved from its initial position to its engaged position, the elongate arm 856 is configured to push the resilient member 809 to cause the flexible arm to deflect, such that the first protrusion 850 engages the cooperating element 854 to hold the needle cover 808 in its retracted position. More particularly, distal movement of the actuation member 824 from its initial position to its engaged position causes a distal end of the elongate arm 856 to engage with the second protrusion 852 of the flexible arm, which causes the flexible arm to be deflected such that the first protrusion 850 engages the cooperating element 854, as shown in FIG. 8C. A proximal-facing edge of the second protrusion 852 may be beveled, to allow the second protrusion 852 and therefore the flexible arm to be forced radially inwards to engage the cooperating element 854 when the proximal-facing edge of the second protrusion 852 is pushed distally by the elongate arm 856.

During proximal translation of the needle sleeve 808 from its extended position shown in FIG. 8A to its retracted position shown in FIG. 8B, the first protrusion 850 is brought into (axial and radial) alignment with the cooperating element 854 of the carrier 822 such that, when the needle cover 808 is in its retracted position shown in FIG. 8C, the flexible arm is able to be deflected by the actuation member 824 to engage the cooperating element 854.

The actuation member 824 may be configured to be moved from its initial position to its engaged position by the user applying an actuation force F to an outer surface of the actuation member 824, such as the actuation surface 827, as shown in FIG. 8C. As an example, the user may apply the actuation force F by pushing the actuation surface 827 of the actuation member 824 with a finger or thumb distally, towards the needle cover 808. The user may apply the actuation force F by making direct contact between their finger 852 and the actuation surface 827. The actuation force F may be a separate force to any force provided by the user to retract the needle cover 808 and/or initiate medicament delivery. In other words, application of the actuation force F may require a separate, distinct movement by the user to any movement used to retract the needle cover 808 and/or initiate medicament delivery.

Where the cooperating element 854 comprises an aperture or recess formed in the needle cover 808, the first protrusion 850 may be dimensioned to have a slightly smaller cross-section than the aperture or recess, for similar reasons as previously described in relation to cooperating element 332 and protrusion 328.

The needle cover 808 is unable to move distally with respect to the body 810 while the actuation member 824 is in its engaged position, regardless of the biasing force exerted on the needle cover 808 by the needle cover biasing member 896. As a result, the biasing force exerted on the needle cover 808 by the needle cover biasing member 896 is not transferred from the needle cover 808 to the injection site. This means that the user is no longer required to overcome the biasing force of the needle cover biasing member 896 while the actuation member 824 is in its engaged position, making it easier for the user to hold the device 800 steady at the injection site.

Figure 8D:
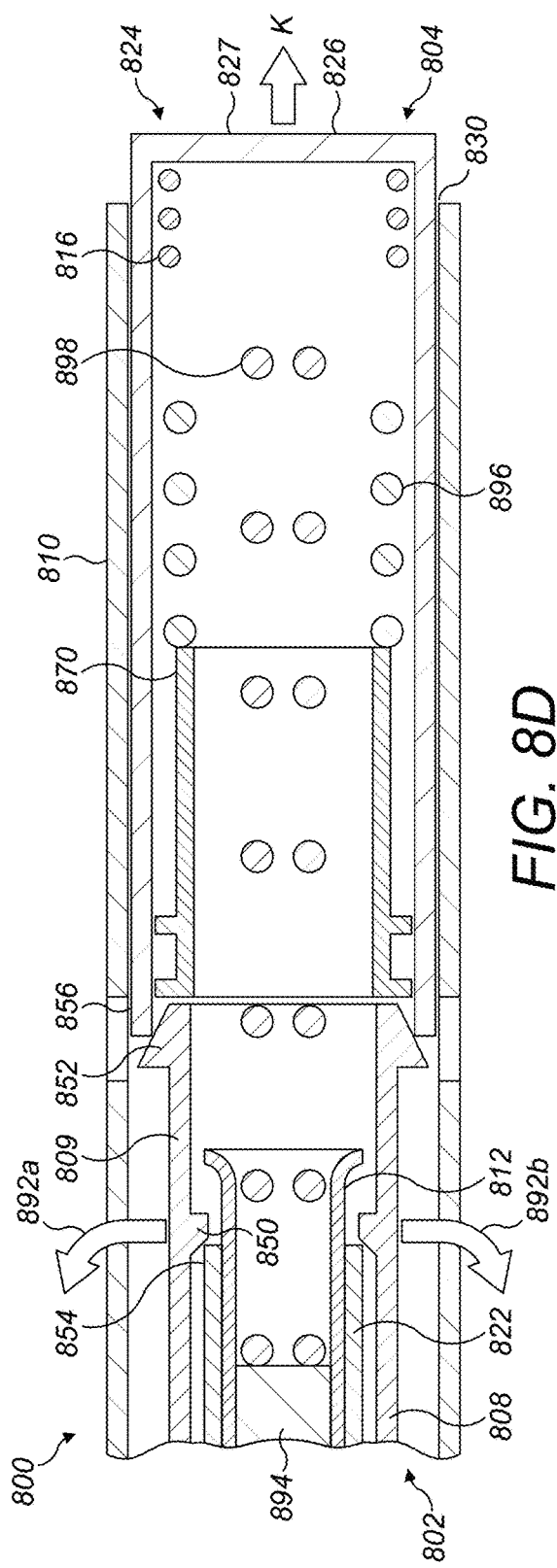
FIG. 8D shows the medicament delivery device of FIG. 8C with the actuation member having returned to the initial position.

After the medicament has been delivered, the user releases the actuation member 824 by removing their finger from the actuation surface 827 and thereby removing the actuation force F applied to the actuation member 824. As shown in FIG. 8D, the actuation member 824 is caused to automatically return from its engaged position to its initial position once the actuation force F is removed, due to the biasing member 816 exerting a biasing force K to bias the actuation member 824 towards its initial position.

In moving the actuation member 824 from its engaged position back to its initial position, deflection of the flexible arm by the elongate arm 856 is reversed (as indicated by pivot arrow 892a) such that the first protrusion 850 becomes disengaged from the cooperating element 854, as shown in FIG. 8D. As such, the needle cover 808 is no longer held in its retracted position by the actuation member 824 and is able to move distally with respect to the body 810. The user may then remove the device 800 from the injection site. Since the needle cover 808 is no longer being held by the actuation member 824, the needle cover 808 moves distally from its retracted position to its initial position under the biasing force of the needle cover biasing member, as the body 810 and needle cover 808 are pulled away from the injection site. The post-use state of the device 800 may appear similar to the pre-use state shown in FIG. 8A, where the needle cover 808 is in its initial position extending from the distal end 802 of the body 810 and covering the needle 806, however the plunger, drive spring and piston will each have been moved distally due to medicament delivery.

FIGS. 8A to 8D show the medicament delivery device 800 comprising a second resilient member arranged opposite the first resilient member 809, about the longitudinal axis of the device 800, and which comprises a first protrusion and a second protrusion similar to the first protrusion 850 and the second protrusion 852 of the first resilient member 809. The second resilient member may be arranged to act in a similar manner to the first resilient member 809, with deflection of the second resilient member by the actuation member 824 indicated by the pivot arrows 890b and 892b being similar to the deflection of the first resilient member 809 indicated by arrows 890a and 892b, but in an opposite direction. It should be understood that in various examples, the medicament delivery device 800 could comprise one resilient member 809, two resilient members 809, or greater than two resilient members 809.

FIGS. 9A to 9D show features of a sixth embodiment of a medicament delivery device 900, which is also referred to herein as an injector device. These Figures each show a cross section of the device 900 during various stages of activation of the device 900. Certain features of the device 900 may have been omitted from FIGS. 9A to 9D for clarity.

The device 900 may have a similar form as a medicament delivery device described previously, having a distal end 902 and a proximal end 904 arranged along a longitudinal axis of the device 900. The device 900 has a needle for injecting medicament into a user at an injection site (such as the user's skin), a needle cover 908 and a body 910 (also known as a housing). The body 910 may be substantially cylindrical and has a substantially constant diameter along the longitudinal axis. The body 910 forms part of the external surface of the device 900 and is configured to be gripped by a user during an injection process.

The device 900 houses a pre-filled syringe 912 containing a medicament and a carrier 922 which supports the pre-filled syringe 912 within the body 910. The needle is in fluid communication with the pre-filled syringe 912 and extends from the distal end of the pre-filled syringe 912. The needle cover 908 is axially movable relative to the body 910 between an initial, extended position, shown in FIG. 9A, in which the needle cover 908 covers (surrounds) the needle, and a retracted position, shown in FIG. 9B, for dispensing medicament from the device 900. In the retracted position, the needle protrudes from the distal end of the needle cover 908.

A needle cover biasing member 996 such as a spring may be arranged in the body 910 (e.g. at a proximal end of the body 910) to exert a biasing force against the needle cover 908 which biases the needle cover 908 axially, in the distal direction. The needle cover biasing member 996 may exert the biasing force against the needle cover 908 via a collar 970 arranged concentrically about the longitudinal axis of the device 900, where the collar 970 is configured to move axially within the device 900 to transfer the biasing force from the needle cover biasing member 996 to the needle cover 908. However, in other examples the collar 970 may not be present and the needle cover biasing member 996 may act directly on the needle cover 908.

Medicament is dispensed from the medicament delivery device 900 via the needle while the needle cover 908 is in the retracted position. An automated dispensing mechanism is triggered to start the dispensing of medicament when the needle cover 908 has moved proximally to reach a predetermined axial position within the body 910. The predetermined position may be located just distally of the retracted position, but in other cases may be located just proximally of the retracted position or may be the same as the retracted position.

The automated dispensing mechanism may comprise a plunger 994 that is automatically released when the needle cover 908 reaches the predetermined axial position. Once the plunger 916 is released, it moves distally within the pre-filled syringe 912 to dispense medicament from the pre-filled syringe 912 through the needle. The plunger 994 may be moved by a driving force provided by a plunger driving mechanism such as a drive spring 998, however other suitable forms of a plunger driving mechanism than a drive spring 998 may instead be used to move the plunger 994, such as an electromechanical motor or a gas cartridge.

In preparation for using the device 900 to administer the medicament, the user may remove a cap from the distal end 902 of the medicament delivery device 900. To initiate medicament delivery, the user presses the needle cover 908 against an injection site such as the user's skin to move the needle cover 908 axially relative to the body 910 in a proximal direction and to uncover the needle. The needle is pushed into the injection site. The automated dispensing mechanism is released, and medicament is automatically dispensed from the device 900 via the needle. The user holds the needle cover 908 in the retracted position whilst the medicament is dispensed.

FIG. 9A shows the device 900 in a pre-use state, which may also be called an initial state or initial position. When the device 900 is in this state, the needle cover 908 is in an extended position with respect to the body 910 in which it covers the needle.

The device 900 comprises an actuation member 924 for holding the needle cover 908 in its retracted position. In the sixth embodiment, the actuation member 924 takes the form of a button arranged to extend through an opening 930 at a proximal end face of the body 910. The actuation member 924 comprises an actuation element 926 having a proximally-facing actuation surface 927, and one or more elongate arms 956 extending distally from a distal-facing surface of the actuation element 926. The one or more elongate arms 956 extend distally within the body 910.

The needle cover 908 comprises a resilient member 909 at a proximal end thereof for engaging with a cooperating element 940 of the medicament delivery device 900. The resilient member 909 may take the form of a flexible arm extending proximally and having a first protrusion 952 and a second protrusion 950 each disposed at a free end of the flexible arm. The first protrusion 952 and second protrusion 950 may each extend from the flexible arm radially outwards towards the body 910.

The actuation member 924, when moved from an initial position to an engaged position, is configured to cause the resilient member 909 to be deflected (as indicated by pivot arrow 992) such that the resilient member 909 engages the cooperating element 940, to hold the needle cover 908 in its retracted position. More particularly, the actuation member 924, when moved from the initial position to the engaged position, is configured to cause flexible arm of the resilient member 909 to be deflected such that the first protrusion 952 engages the cooperating element 940, to hold the needle cover 908 in its retracted position.

The flexible arm is movable between a first position (shown in FIG. 9C), in which the first protrusion 952 engages the cooperating element 940 to hold the needle cover in its retracted position, and a second position (shown in FIG. 9B), in which the protrusion is disengaged from the cooperating element 940. The flexible arm is biased to deflect from its second position to its first position, due to the resilient nature of the flexible arm. The elongate arm 956 is configured to hold the flexible arm in its second position when the actuation member 924 is in its initial position (as shown in FIG. 9B), and is configured to release the flexible arm to deflect to its first position when the actuation member 924 is in its engaged position (as shown in FIG. 9C).

The cooperating element 940 may take the form of an aperture, a recess, a ridge, or a frictional surface. FIG. 9A shows the cooperating element 940 formed at the body 910, the cooperating element 940 comprising an aperture in the body 910.

FIG. 9A shows the actuation member 924 in its initial position. The actuation member 924 may be biased into the initial position by a biasing member 916 such as a spring. While the actuation member 924 is in its initial position, the resilient member 909 is disengaged from the cooperating element 940, thereby allowing the needle cover 908 to axially move back and forth between its retracted position and its extended position. More specifically, while the actuation member 924 is in its initial position, the first protrusion 952 of the flexible arm is disengaged from the cooperating element 940 formed at the body 910, thereby allowing the needle cover 908 to axially move back and forth between its retracted position and its extended position.

As shown in FIG. 9A, when the needle cover 908 is in its extended position with respect to the body 910, the first protrusion 952 of the resilient member 909 is not in alignment with the cooperating element 940. Due to this misalignment, the first protrusion 952 cannot engage the cooperating element 940 to hold the needle cover 908 relative to the body 910 while the needle cover 908 is in its extended position.

FIG. 9B shows the device 900 in an activated state. To transition the device 900 from the initial state shown in FIG. 9A to the activated state shown in FIG. 9B, a distal force is applied via the body 910 while the needle cover 908 is placed against the injection site, such as the user's skin, causing the needle cover 908 to move proximally into the device 900 against the biasing force of the needle cover biasing member 996.

When the device 900 is in the activated state as shown in FIG. 9B, the needle cover 908 is fully displaced into the device 900 and is in its retracted position. The needle protrudes from the end of the needle cover 908 to its maximum extent. The medicament dispensing mechanism of the device 900 is triggered. In this example, triggering of the dispensing mechanism comprises the drive spring 998 being released such that the drive spring 998 expands from a compressed state to an extended state, applying a distal force to a plunger 994 of the pre-filled syringe 912. The distal force causes the plunger 994 to move distally and in turn cause medicament to be expelled from the pre-filled syringe 912 via the needle.

To overcome the biasing force of the needle cover biasing member 996, the user can actuate the actuation member 924 while the needle cover 908 is in its retracted position such that the actuation member 924 moves distally from its initial position shown in FIG. 9B to its engaged position shown in FIG. 9C.

During proximal translation of the needle sleeve 908 from its extended position shown in FIG. 9A to its retracted position shown in FIG. 9B, the first protrusion 952 is brought into (axial and radial) alignment with the cooperating element 940 such that, when the needle cover 908 is in its retracted position shown in FIG. 9C, the flexible arm is able to be deflected by the actuation member 924 to engage the cooperating element 940.

When the actuation member 924 is in its initial position (for example as shown in FIG. 9B), the second protrusion 950 abuts an inner surface of the elongate arm 956, preventing the flexible arm from deflecting radially outwards toward the body 910. As such, the first protrusion 952 remains disengaged from the cooperating element 940 and so the needle cover 908 can be axially moved between its retracted position and its extended position. However, when the actuation member 924 is moved from its initial position to its engaged position, the elongate arm 956 is configured to move axially such that an aperture 942 in the elongate arm 956 is aligned with the second protrusion 950. When the actuation member 924 is in its engaged position, the second protrusion 950 is configured to enter the aperture 942, thereby allowing the flexible arm to deflect radially outwards and towards the body 910 due to the resilient nature of the flexible arm, bringing the first protrusion 952 into engagement with the cooperating element 940 to hold the needle cover 908 in its retracted position.

The actuation member 924 may be configured to be moved from its initial position to its engaged position by the user applying an actuation force F to an outer surface of the actuation member 924, such as the actuation surface 927, as shown in FIG. 9C. As an example, the user may apply the actuation force F by pushing the actuation surface 927 of the actuation member 924 with a finger or thumb distally, towards the needle cover 908. The user may apply the actuation force F by making direct contact between their finger 952 and the actuation surface 927. The actuation force F may be a separate force to any force provided by the user to retract the needle cover 908 and/or initiate medicament delivery. In other words, application of the actuation force F may require a separate, distinct movement by the user to any movement used to retract the needle cover 908 and/or initiate medicament delivery.

Where the cooperating element 940 comprises an aperture or recess, the first protrusion 952 may be dimensioned to have a slightly smaller cross-section than the aperture or recess, for similar reasons as previously described in relation to cooperating element 332 and protrusion 328.

The needle cover 908 is unable to move distally with respect to the body 910 while the actuation member 924 is in its engaged position, regardless of the biasing force exerted on the needle cover 908 by the needle cover biasing member 996. As a result, the biasing force exerted on the needle cover 908 by the needle cover biasing member 996 is not transferred from the needle cover 908 to the injection site. This means that the user is no longer required to overcome the biasing force of the needle cover biasing member 996 while the actuation member 924 is in its engaged position, making it easier for the user to hold the device 900 steady at the injection site.

After the medicament has been delivered, the user releases the actuation member 924 by removing their finger from the actuation surface 927 and thereby removing the actuation force F applied to the actuation member 924. As shown in FIG. 9D, the actuation member 924 is caused to automatically return from its engaged position to its initial position once the actuation force F is removed, due to the biasing member 916 exerting a biasing force K to bias the actuation member 924 towards its initial position.

In moving the actuation member 924 from its engaged position back to its initial position, deflection of the flexible arm is reversed (as indicated by pivot arrow 992a in FIG. 9D) such that the first protrusion 952 becomes disengaged from the cooperating element 940. This may be achieved by a distal-facing edge of the second protrusion 950 being beveled, to allow the second protrusion 950 (and therefore the flexible arm) to be forced radially inwards by engagement of the distal-facing edge with a proximal-facing edge of the aperture 942 as the elongate arm 956 moves proximally. Once the actuation member 924 has returned to its initial position and the flexible arm has returned to its second position, the needle cover 908 is no longer held in its retracted position by the actuation member 924 and is able to move distally with respect to the body 910.

The user may then remove the device 900 from the injection site. Since the needle cover 908 is no longer being held by the actuation member 924, the needle cover 908 moves distally from its retracted position to its initial position under the biasing force of the needle cover biasing member, as the body 910 and needle cover 908 are pulled away from the injection site. The post-use state of the device 900 may appear similar to the pre-use state shown in FIG. 9A, where the needle cover 908 is in its initial position extending from the distal end 902 of the body 910 and covering the needle 906, however the plunger, drive spring and piston will each have been moved distally due to medicament delivery.

Figure 10A:
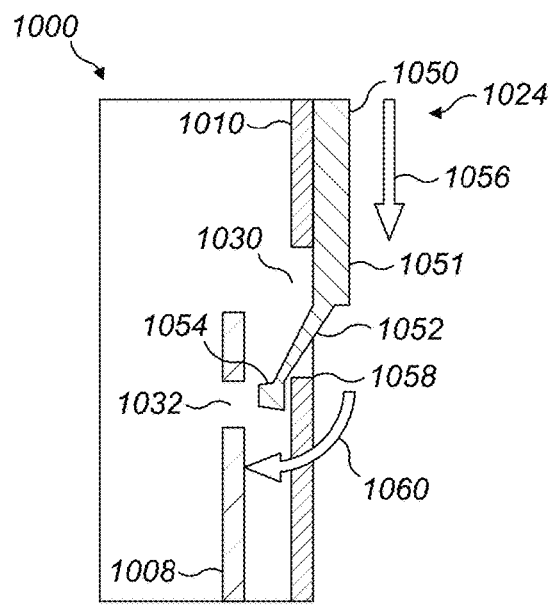
FIG. 10A shows portions of a medicament delivery device according to a seventh embodiment with an actuation member in an initial position.
Figure 10B:
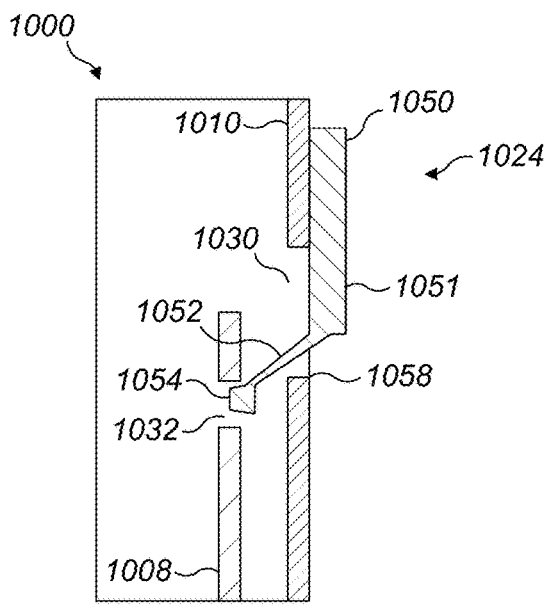
FIG. 10B shows portions of the medicament delivery device of FIG. 10A with the actuation member in an engaged position.

FIGS. 10A and 10B show features of a seventh embodiment of a medicament delivery device 1000, which is also referred to herein as an injector device. These Figures each show a cross section of a portion of a needle cover 1008 and a body 1010 of the device 1000.

FIG. 10A shows a close up of an actuation member 1024 and the region of the needle cover 1008 with which it interacts. The other parts of the medicament delivery device 1000 may be the same as those shown and described in the preceding embodiments.

FIG. 10A shows the device 1000 in an activated state in which the needle cover 1008 is in a retracted position within the body 1010 to expose the needle. The needle cover 1008 may have been moved from an extended position (in which it covers the needle) to its retracted position by any manner described herein. A needle cover biasing member may bias the needle cover 1008 from its retracted position to its extended position. The actuation member 1024 takes the form of a slider arranged at the body 1010. The slider comprises a slider body 1050 arranged at an outer surface of the body 1010, a resilient arm 1052 extending from the slider body 1050 through an aperture 1030 in the body 1010, and a protrusion 1054 disposed at a free end of the resilient arm 1052 between an inner surface of the body 1010 and an outer surface of the needle cover 1008.

FIG. 10A shows the actuation member 1024 in an initial position in which the protrusion 1054 is disengaged from a cooperating element 1032 disposed on the needle cover 1008. As such, the needle cover 1008 remains free to be axially moved between its retracted position and its extended position. The cooperating element 1032 may take the form of an aperture, a recess, a ridge or a frictional surface.

The slider body 1050 may be slidably coupled to the body 1010. The actuation member 1024 is configured to be moved from its initial position to its engaged position by a user applying a sliding force 1056 to the slider body 1050 (e.g. to an actuation surface 1051 of the slider body 1050) to slide the slider body 1050 towards the aperture 1030. As the slider body 1050 is moved towards the aperture 1030, the resilient arm 1052 is deflected by an edge 1058 of the aperture 1030, causing the resilient arm 1052 to pivot towards the needle cover 1032 as indicated by the pivot arrow 1060, and therefore causing the protrusion 1054 to engage the cooperating element 1032 disposed on the needle cover.

FIG. 10B shows the actuation member 1024 in its engaged position, where the needle cover 1030 is held in its retracted position by the engagement between the protrusion 1054 and the cooperating element 1032. The actuation member 1024 may be moved back to its initial position by moving the slider body 1050 in the opposite direction to previously, causing the protrusion 1054 to disengage from the cooperating element 1032 such that the needle cover 1008 is no longer held in its retracted position. In some examples, the resilient arm 1052 may act as a biasing member to bias the actuation member 1024 from its engaged position towards its initial position by applying a biasing force. In such examples, the user may move the actuation member 1024 from its engaged position to its initial position simply by releasing the slider body 1050 (i.e. the user no longer applying a sliding force to the slider body 1050) to allow the actuation member 1024 to automatically move from its engaged position to its initial position due to the biasing force.

Figure 11A:
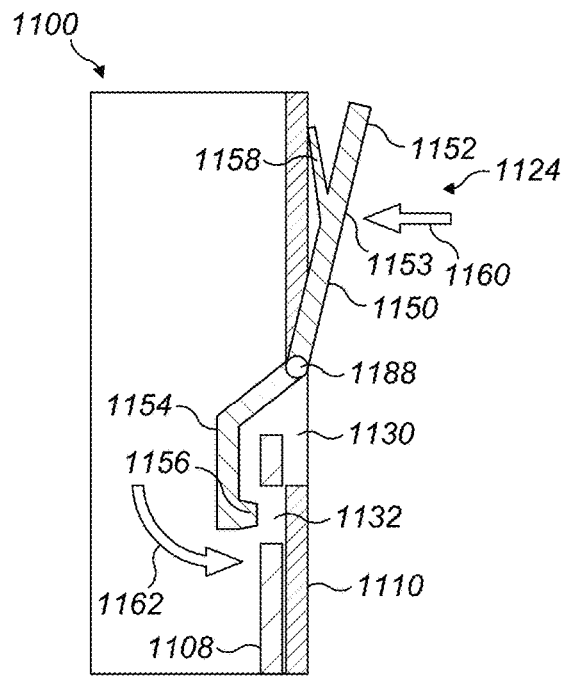
FIG. 11A shows portions of a medicament delivery device according to an eighth embodiment with an actuation member in an initial position.
Figure 11B:
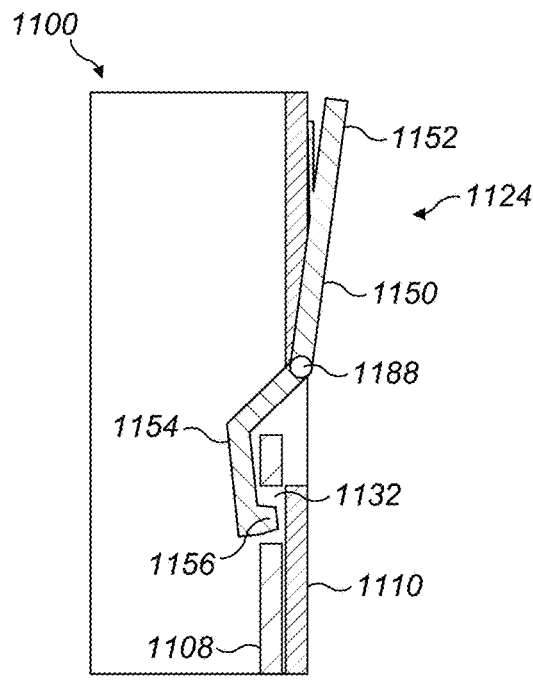
FIG. 11B shows portions of the medicament delivery device of FIG. 11A with the actuation member in an engaged position.

FIGS. 11A and 11B show features of a eighth embodiment of a medicament delivery device 1100, which is also referred to herein as an injector device. These Figures each show a cross section of a portion of a needle cover 1108 and a body 1110 of the device 1100.

FIG. 11A shows a close up of an actuation member 1124 and the region of the needle cover 1108 with which it interacts. The other parts of the medicament delivery device 1100 may be the same as those shown and described in the preceding embodiments.

FIG. 11A shows the device 1100 in an activated state in which the needle cover 1108 is in a retracted position within the body 1110 to expose the needle. The needle cover 1108 may have been moved from an extended position (in which it covers the needle) to its retracted position by any manner described herein. A needle cover biasing member may bias the needle cover 1108 from its retracted position to its extended position. The actuation member 1124 takes the form of a pivotable arm 1150 arranged at the body 1110. The pivotable arm 1150 is arranged to extend through an aperture 1130 in the body 1110. The pivotable arm 1150 comprising a first arm portion 1152 arranged outside the body 1110, a second arm portion 1154 arranged inside the body 1110 and having a protrusion 1156 disposed at a free end of the second arm portion 1154, and a pivot 1188 arranged between the first arm portion 1152 and the second arm portion 1154.

FIG. 11A shows the actuation member 1124 in an initial position in which the protrusion 1156 is disengaged from a cooperating element 1132 disposed on the needle cover 1108. As such, the needle cover 1108 remains free to be axially moved between its retracted position and its extended position. The cooperating element 1132 may take the form of an aperture, a recess, a ridge or a frictional surface.

The actuation member 1124 is configured to be moved from its initial position shown in FIG. 11A to an engaged position shown in FIG. 11B by a user applying an actuation force 1160 to the first arm portion 1152 (e.g. to an actuation surface 1153 of the first arm portion 1152) to cause the first arm portion 1152 and the second arm portion 1154 to rotate about the pivot 1188, as indicated by pivot arrow 1162. The first arm portion 1152 and the second arm portion 1154 are caused to rotate such that the protrusion 1156 disposed at the free end of the second arm portion 1154 is brought into engagement with the cooperating element 1132 disposed on the needle cover 1108, to hold the needle cover 1108 in its retracted position.

FIG. 11B shows the actuation member 1124 in its engaged position, where the needle cover 1130 is held in its retracted position by the engagement between the protrusion 1156 and the cooperating element 1132. The actuation member 1124 may be moved back to its initial position by a user moving first arm portion 1152 in the opposite direction to previously, causing the protrusion 1156 to disengage from the cooperating element 1132 such that the needle cover 1108 is no longer held in its retracted position. In some examples, a biasing member 1158 such as a leaf spring may be arranged to bias the actuation member 1124 from its engaged position towards its initial position by applying a biasing force. In such examples, the user may move the actuation member 1124 from its engaged position to its initial position simply by releasing the first arm portion 1152 (i.e. the user no longer applying an actuation force 1160 to the first arm portion 1152) to allow the actuation member 1124 to automatically move from its engaged position to its initial position due to the biasing force.

FIGS. 12A and 12B show features of an ninth embodiment of a medicament delivery device 1200, which is also referred to herein as an injector device. These Figures each show a cross section of a portion of a needle cover 1208 and a body 1210 of the device 1200, as viewed along the longitudinal axis of the device 1200.

FIG. 12A shows a close up of an actuation member 1224 and the region of the needle cover 1208 with which it interacts. The other parts of the medicament delivery device 1200 may be the same as those shown and described in the preceding embodiments.

FIG. 12A shows the device 1200 in an activated state in which the needle cover 1208 is in a retracted position within the body 1210 to expose the needle. The needle cover 1208 may have been moved from an extended position (in which it covers the needle) to its retracted position by any manner described herein. A needle cover biasing member may bias the needle cover 1208 from its retracted position to its extended position. The actuation member 1224 takes the form of a rotatable collar 1250 arranged at the body 1210. The rotatable collar 1250 is arranged to surround an outer surface of the body 1210 such that the rotatable collar 1250 is concentric with the body 1210 about the longitudinal axis of the device 1200. The rotatable collar 1250 comprises a protrusion 1252 disposed on an inner surface of the rotatable collar 1250, the protrusion 1252 extending through an aperture in the body 1210.

FIG. 12A shows the actuation member 1224 in an initial position in which the protrusion 1252 is disengaged from a cooperating element disposed on the needle cover 1208. As such, the needle cover 1208 remains free to be axially moved between its retracted position and its extended position. The cooperating element may take the form of an aperture, a recess, a ridge or a frictional surface.

The actuation member 1224 is configured to be moved from its initial position shown in FIG. 12A to an engaged position shown in FIG. 12B by a user rotating the rotatable collar 1250 about the body 1210 such that the protrusion 1252 is brought into engagement with the cooperating element disposed on the needle cover 1208, to hold the needle cover 1208 in its retracted position. The user may rotate the rotatable collar 125 by applying a rotation force 1270 to the rotatable collar 1250 (e.g. to an actuation surface 1251 of the rotatable collar 1250) to cause the rotatable collar 1250 to rotate about the longitudinal axis of the device 1200 relative to the body 1210 and needle cover 1208.

FIG. 12B shows the actuation member 1224 in its engaged position, where the needle cover 1230 is held in its retracted position by the engagement between the protrusion 1252 and the cooperating element. The actuation member 1224 may be moved back to its initial position by a user rotating the rotatable collar 1250 in the opposite direction to previously, causing the protrusion 1252 to disengage from the cooperating element such that the needle cover 1208 is no longer held in its retracted position. In some examples, a biasing member such as a spring may be arranged to bias the actuation member 1124 from its engaged position towards its initial position by applying a biasing force. In such examples, the user may move the actuation member 1224 from its engaged position to its initial position simply by releasing the rotatable collar 1250 (i.e. the user no longer applying a rotation force 1270 to the rotatable collar 1250) to allow the actuation member 1224 to automatically move from its engaged position to its initial position due to the biasing force.

FIGS. 13A and 13B show features of a tenth embodiment of a medicament delivery device 1300, which is also referred to herein as an injector device. These Figures each show a cross section of a portion of a needle cover 1308 and a body 1310 of the device 1300.

FIG. 13A shows a close up of an actuation member 1324 and the region of the needle cover 1308 with which it interacts. The other parts of the medicament delivery device 1300 may be the same as those shown and described in the preceding embodiments.

FIG. 13A shows the device 1300 in an activated state in which the needle cover 1308 is in a retracted position within the body 1310 to expose the needle. The needle cover 1308 may have been moved from an extended position (in which it covers the needle) to its retracted position by any manner described herein. A needle cover biasing member may bias the needle cover 1308 from its retracted position to its extended position. The actuation member 1324 takes the form of a resilient portion 1312 of the body 1310 and a protrusion 1314 formed on an inner surface of the resilient portion 1312 of the body 1310, the protrusion 1314 extending into the device 1300, towards the needle cover 1308.

FIG. 13A shows the actuation member 1324 in an initial position in which the protrusion 1314 is disengaged from a cooperating element 1332 disposed on the needle cover 1308. As such, the needle cover 1308 remains free to be axially moved between its retracted position and its extended position. The cooperating element 1332 may take the form of an aperture, a recess, a ridge or a frictional surface.

The actuation member 1324 is configured to be moved from its initial position shown in FIG. 13A to an engaged position shown in FIG. 13B by a user applying an actuation force 1370 to an outer surface (e.g. actuation surface 1313) of the resilient portion 1312 of the body 1310 such that the resilient portion 1312 of the body 1310 is deflected inwards, to cause the protrusion 1314 to engage the cooperating element 1332 disposed on the needle cover 1308 and therefore hold the needle cover 1308 in its retracted position.

Since the resilient portion 1312 of the body 1310 acts as biasing member to bias the actuation member 1324 from its engaged position towards its initial position by applying a biasing force, the user may move the actuation member 1324 from its engaged position to its initial position simply by releasing the resilient portion 1312 (i.e. the user no longer applying an actuating force to the resilient portion 1312), to allow the actuation member 1324 to automatically move from its engaged position to its initial position due to the biasing force.

Figure 14:
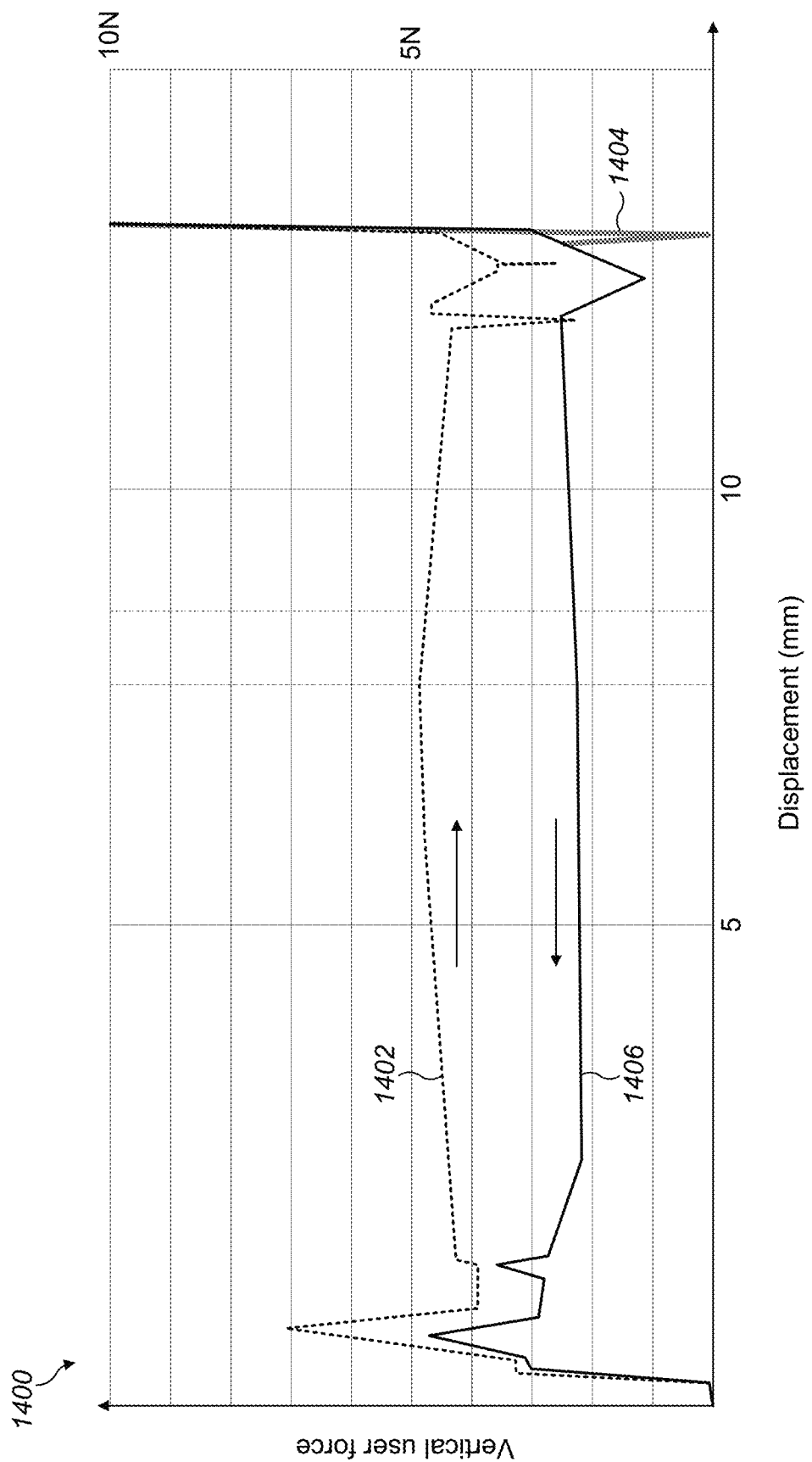
FIG. 14 is a force profile graph illustrating the force profile of a first device and the medicament delivery devices according to the first to tenth embodiments.

Referring to FIG. 14, a force profile graph 1400 is shown illustrating the force profile of a medicament delivery device, such as any of the medicament delivery devices 300, 400, 600, 700, 800, 900, 1000, 1100, 1200 or 1300 described herein. The horizontal axis is the displacement of the needle cover of the device in millimeters (mm) and the vertical axis is the user applied force in Newtons (N).

The first trace 1402 shows the force profile of the activation force of a medicament delivery device, such as any of the medicament delivery devices 300, 400, 600, 700, 800, 900, 1000, 1100, 1200 or 1300, when the user is pushing the device onto an injection site. The second trace 1406 shows the force profile of the medicament delivery device when the user is removing the medicament delivery device from the injection site after completion of medicament delivery, where the user has not utilized the actuation member of the medicament delivery device during medicament delivery. In other words, the user has not moved the actuation member of the medicament delivery device from its initial position to its engaged position at any point during the injection procedure. As such, the needle cover biasing member continues to apply a non-zero biasing force to the needle while the needle cover is at its maximum displacement within the body, as indicated by the second trace 1406. This biasing force is matched by a corresponding vertical user force if the user is to hold the medicament delivery device steady at an injection site.

In order to overcome the biasing force of the needle cover biasing member, the user may instead utilize the actuation member of the medicament delivery device during medicament delivery. In other words, the user may move the actuation member of the medicament delivery device from its initial position to its engaged position while the needle cover is at its maximum displacement, before moving the actuation member back to its initial position once medicament delivery is complete.

The third trace 1404 shows a modification to the force profile of the second trace 1406 which occurs when the user has instead utilized the actuation member during medicament delivery. The user has moved the actuation member of the medicament delivery device from its initial position to its engaged position while the needle cover is at its maximum displacement such that the needle cover biasing member no longer exerts a biasing force on the needle cover. This is shown in FIG. 14 by the third trace 1404 indicating a zero vertical user force near the maximum displacement of the needle cover. The user therefore is therefore no longer required to provide a corresponding vertical user force to overcome a biasing force of the needle cover biasing member if the user is to hold the medicament delivery device steady at an injection site. Once medicament delivery is complete, the user moves the actuation member back to its initial position to release the needle cover, after which the force profile of the medicament delivery device will once again follow the second trace 1406 as the medicament delivery device is removed from the injection site.

While embodiments have been generally disclosed herein in which an actuation member engages with a needle cover to hold the needle cover in its retracted position, it should be noted that in other embodiments the actuation member may be arranged to engage with an intermediate member that is used to transfer the biasing force from the needle cover biasing means to the needle cover, to hold that intermediate member relative to the body of the medicament delivery device.

The intermediate member may comprise a collar, for example, such as the collar 870 or collar 970 previously described in relation to FIGS. 8A to 8D and FIGS. 9A to 9D. The needle cover biasing means may be arranged to provide the biasing force to the intermediate member, which in turn provides the biasing force to the needle cover. In such examples, the actuation member may be arranged to engage with the collar when in its engaged position to hold the collar and prevent the collar from moving distally. As such, the collar is unable to transfer the biasing force of the needle cover biasing means to the needle cover while the actuation member is in its engaged position.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g., a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu (B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N—(N-lithocholyl-gamma-glutamyl)-des(B30) human insulin; B29-N—(ω-carboxyheptadecanoyl)-des(B30) human insulin and B29-N—(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C (Efpeglenatide), HM-15211, CM-3, GLP-1 Eligen, ORMD-0901, NN-9423, NN-9709, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, ZP-DI-70, TT-401

(Pegapamodtide), BHM-034, MOD-6030, CAM-2036, DA-15864, ARI-2651, ARI-2255, Tirzepatide (LY3298176), Bamadutide (SAR425899), Exenatide-XTEN and Glucagon-Xten.

An example of an oligonucleotide is, for example: mipomersen sodium (Kynamro®), a cholesterol-reducing antisense therapeutic for the treatment of familial hypercholesterolemia or RG012 for the treatment of Alport syndrom. Examples of DPP4 inhibitors are Linagliptin, Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present invention include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present invention, which encompass such modifications and any and all equivalents thereof.

An example drug delivery device may involve a needle-based injection system as described in Table 1 of section 5.2 of ISO 11608-1:2014(E). As described in ISO 11608-1:2014 (E), needle-based injection systems may be broadly distinguished into multi-dose container systems and single-dose (with partial or full evacuation) container systems. The container may be a replaceable container or an integrated non-replaceable container.

As further described in ISO 11608-1:2014(E), a multi-dose container system may involve a needle-based injection device with a replaceable container. In such a system, each container holds multiple doses, the size of which may be fixed or variable (pre-set by the user). Another multi-dose container system may involve a needle-based injection device with an integrated non-replaceable container. In such a system, each container holds multiple doses, the size of which may be fixed or variable (pre-set by the user).

As further described in ISO 11608-1:2014(E), a single-dose container system may involve a needle-based injection device with a replaceable container. In one example for such a system, each container holds a single dose, whereby the entire deliverable volume is expelled (full evacuation). In a further example, each container holds a single dose, whereby a portion of the deliverable volume is expelled (partial evacuation). As also described in ISO 11608-1:2014 (E), a single-dose container system may involve a needle-based injection device with an integrated non-replaceable container. In one example for such a system, each container holds a single dose, whereby the entire deliverable volume is expelled (full evacuation). In a further example, each container holds a single dose, whereby a portion of the deliverable volume is expelled (partial evacuation).

Those of skill in the art will understand that modifications (additions and/or removals) of various components of the embodiments described herein may be made without departing from the full scope and spirit of the present invention, which encompass such modifications and any and all equivalents thereof.

LIST OF REFERENCE NUMBERS

10—drug delivery device
11—housing
11a—window
12—cap
13—needle sleeve
14—reservoir
15—medicament
17—needle
20—distal region
21—proximal region
22—button
23—bung or piston
103—device body
104—spring
110—device
113—needle cover
115—injection site
117—needle
120—holding force
125—spring force
300—medicament delivery device
302—distal end
304—proximal end
306—needle
308—needle cover
310—body
312—pre-filled syringe
314—needle cover biasing member
316—plunger
318—drive spring
320—bung or piston
322—carrier
324—actuation member
326—actuation element
327—actuation surface
328—protrusion
330—aperture
332—cooperating element
350—hand
352—finger
400—medicament delivery device
402—distal end
404—proximal end
406—needle
408—needle cover
410—body
412—pre-filled syringe
422—carrier
424—actuation member
426—actuation element
427—actuation surface
428—protrusion
430—aperture
432—cooperating element
504—flexible portion
510—recess
600—medicament delivery device
602—distal end
604—proximal end
606—needle
608—needle cover
610—body
612—pre-filled syringe
622—carrier
624—actuation member
626—actuation element
627—actuation surface
628—protrusion
630—aperture
632—cooperating element
650—stopping protrusion
652—biasing member
700—medicament delivery device
702—distal end
704—proximal end
706—needle
708—needle cover
710—body
712—pre-filled syringe
722—carrier
724—actuation member
726—actuation element
727—actuation surface
728—protrusion
730—aperture
732—cooperating element
750a, 750b—flexible portions
800—medicament delivery device
802—distal end
804—proximal end
808—needle cover
809—resilient member
810—body
812—pre-filled syringe
816—biasing member
822—carrier
824—actuation member
826—actuation element
827—actuation surface
830—opening
850—first protrusion
852—second protrusion
854—cooperating element
856—elongate arm
870—collar
890a—pivot arrow
890b—pivot arrow
892a—pivot arrow
892b—pivot arrow
894—plunger
896—needle cover biasing member
898—drive spring
900—medicament delivery device
902—distal end
904—proximal end
908—needle cover
909—resilient member
910—body
912—pre-filled syringe
922—carrier
924—actuation member
926—actuation element
927—actuation surface
930—opening
940—cooperating element
942—aperture
950—second protrusion
952—first protrusion
956—elongate arm
970—collar
992—pivot arrow
994—plunger 996—needle cover biasing member
997—pivot arrow
998—drive spring
1000—medicament delivery device
1008—needle cover
1010—body
1024—actuation member
1030—aperture
1032—cooperating element
1050—slider body
1051—actuation surface
1052—resilient arm
1054—protrusion
1056—sliding force
1058—edge
1060—pivot arrow
1100—medicament delivery device
1108—needle cover
1110—body
1124—actuation member
1130—aperture
1132—cooperating element
1150—pivotable arm
1152—first arm portion
1153—actuation surface
1154—second arm portion
1156—protrusion
1158—biasing member
1160—actuation force
1162—pivot arrow
1188—pivot
1200—medicament delivery device
1208—needle cover
1210—body
1224—actuation member
1250—rotatable collar
1251—actuation surface
1252—protrusion
1270—rotation force
1300—medicament delivery device
1308—needle cover
1310—body
1312—resilient portion
1313—actuation surface
1314—protrusion
1324—actuation member
1332—cooperating element
1370—actuating force
1400—force profile graph
1402—first trace
1404—third trace
1406—second trace

The invention claimed is:

1. A medicament delivery device comprising:
a needle for injecting medicament, the needle disposed at a distal end of the medicament delivery device;
a body for containing a syringe;
a needle cover axially movable relative to the body between an extended position, in which a distal end of the needle cover is distal to a distal end of the needle, and a retracted position for dispensing a medicament from the medicament delivery device, wherein the distal end of the needle is distal to the distal end of the needle cover when the needle cover is in the retracted position; and
an actuation member arranged at an outer circumferential surface of the body, the actuation member being configured to be movable by a user from an initial position to an engaged position by causing the actuation member to move radially into the body,
wherein, when the actuation member is in the initial position, the needle cover is axially movable between the retracted position and the extended position, and when the actuation member is in the engaged position, the actuation member engages with the needle cover to hold the needle cover in the retracted position.

2. The medicament delivery device of claim 1, further comprising a biasing member configured to bias the actuation member from the engaged position to the initial position.

3. The medicament delivery device of claim 1, wherein the actuation member is configured to be moved from the initial position to the engaged position by the user applying a force to an outer surface of the actuation member.

4. The medicament delivery device of claim 1, wherein the actuation member comprises a button arranged at an outer surface of the body.

5. The medicament delivery device of claim 1, wherein:
the actuation member comprises a protrusion;
the needle cover comprises a cooperating element;
the protrusion is engaged with the cooperating element when the actuation member is in the engaged position to hold the needle cover in the retracted position; and
the protrusion is disengaged from the cooperating element when the actuation member is in the initial position such that the needle cover is axially movable between the retracted position and the extended position.

6. The medicament delivery device of claim 5, wherein the protrusion is configured to engage a distal-facing side of the cooperating element when the actuation member is in the engaged position to hold the needle cover in the retracted position.

7. The medicament delivery device of claim 1, wherein the needle cover comprises a resilient member for engaging with a cooperating element of the medicament delivery device, wherein when the actuation member is moved from the initial position to the engaged position, the actuation member is configured to cause the resilient member to be deflected such that the resilient member engages the cooperating element to hold the needle cover in the retracted position.

8. The medicament delivery device of claim 7, wherein:
the resilient member comprises a flexible arm and a protrusion disposed on a free end of the flexible arm; and
the actuation member comprises an elongate arm configured to push the flexible arm when the actuation member is moved from the initial position to the engaged position to cause the flexible arm to deflect such that the protrusion engages the cooperating element to hold the needle cover in the retracted position.

9. The medicament delivery device of claim 7, wherein:
the resilient member comprises a flexible arm and a protrusion disposed on a free end of the flexible arm;
the actuation member comprises an elongate arm;
the body comprises the cooperating element;
the flexible arm is movable between a first position, in which the protrusion engages the cooperating element to hold the needle cover in the retracted position, and a second position, in which the protrusion is disengaged from the cooperating element;
the flexible arm is biased to deflect from the second position to the first position;

the elongate arm is configured to hold the flexible arm in the second position when the actuation member is in the initial position; and the elongate arm is configured to release the flexible arm to deflect to the first position when the actuation member is in the engaged position.

10. The medicament delivery device of claim 1, wherein the actuation member comprises a slider comprising:
a slider body arranged at an outer surface of the body;
a resilient arm extending from the slider body through an aperture in the body; and
a protrusion disposed at a free end of the resilient arm between an inner surface of the body and an outer surface of the needle cover,
wherein the actuation member is configured to be moved from the initial position to the engaged position by the user sliding the slider body towards the aperture in the body such that the resilient arm is deflected by an edge of the aperture to cause the protrusion to engage a cooperating element disposed on the needle cover to hold the needle cover in its retracted position.

11. The medicament delivery device of claim 1, wherein the actuation member comprises a pivotable arm arranged to extend through an aperture in the body, the pivotable arm comprising:
a first arm portion arranged external to the body;
a second arm portion arranged inside the body and having a protrusion disposed at a free end of the second arm portion; and
a pivot arranged between the first arm portion and the second arm portion,
wherein the actuation member is configured to be moved from the initial position to the engaged position by the user applying a force to the first arm portion to cause the first arm portion and the second arm portion to rotate about the pivot such that the protrusion disposed at the free end of the second arm portion is brought into engagement with a cooperating element disposed on the needle cover to hold the needle cover in the retracted position.

12. The medicament delivery device of claim 1, wherein the actuation member comprises a rotatable collar arranged to surround an outer surface of the body, the rotatable collar comprising a protrusion disposed on an inner surface of the rotatable collar, the protrusion extending through an aperture in the body,
wherein the actuation member is configured to be moved from the initial position to the engaged position by the user rotating the rotatable collar about the body such that the protrusion is brought into engagement with a cooperating element disposed on the needle cover to hold the needle cover in the retracted position.

13. The medicament delivery device of claim 1, wherein the actuation member comprises a resilient portion of the body and a protrusion formed on an inner surface of the resilient portion of the body,
wherein the actuation member is configured to be moved from the initial position to the engaged position by the user applying a force to an outer surface of the resilient portion of the body such that the resilient portion of the body is deflected to cause the protrusion to engage a cooperating element disposed on the needle cover to hold the needle cover in the retracted position.

14. The medicament delivery device of claim 1, further comprising a needle cover biasing member configured to exert a force which biases the needle cover axially towards the distal end of the medicament delivery device.

15. The medicament delivery device of claim 1, further comprising the syringe containing the medicament.

16. A medicament delivery device comprising:
a body for containing a syringe;
a needle cover axially movable relative to the body between an extended position, in which a distal end of the needle cover is distal to a distal end of a needle coupled to the syringe, and a retracted position, in which the distal end of the needle is distal to the distal end of the needle cover; and
a button configured to be actuated by a user to hold the needle cover in the retracted position,
wherein the button is arranged at an outer circumferential surface of the body, and the medicament delivery device is configured such that actuation of the button causes the button to move radially into the body to hold the needle cover.

17. The medicament delivery device of claim 16, wherein the button is configured to be actuated such that the button moves from (i) an initial position, in which the needle cover is axially movable between the retracted position and the extended position, to (ii) an engaged position, in which the button holds the needle cover in the retracted position.

18. The medicament delivery device of claim 17, further comprising a biasing member configured to bias the button from the engaged position to the initial position.

19. The medicament delivery device of claim 16, wherein the button is configured to be actuated by the user applying a force to an outer surface of the button.

20. The medicament delivery device of claim 16, wherein the button is arranged to extend through an opening at a proximal end face of the body, and the medicament delivery device is configured such that actuation of the button causes the button to move axially into the body to hold the needle cover.

21. The medicament delivery device of claim 16, wherein the button is integrally formed with the body.

22. The medicament delivery device of claim 16, wherein the needle cover is arranged to (i) prevent the button from being actuated when the needle cover is in the extended position, and (ii) allow the button to be actuated when the needle cover is in the retracted position.

23. The medicament delivery device of claim 16, wherein:
the button comprises a protrusion; and
the needle cover comprises a cooperating element, and
wherein the medicament delivery device is configured such that the actuation of the button causes the protrusion to engage the cooperating element to hold the needle cover in the retracted position.

24. The medicament delivery device of claim 23, wherein the cooperating element comprises an aperture, a recess, a ridge, or a frictional surface.

25. The medicament delivery device of claim 16, wherein the needle cover comprises a resilient member for engaging with a cooperating element of the medicament delivery device, and the medicament delivery device is configured such that actuation of the button causes the resilient member to be deflected such that the resilient member engages the cooperating element to hold the needle cover in the retracted position.

26. The medicament delivery device of claim 25, wherein:
the resilient member comprises a flexible arm and a protrusion disposed on a free end of the flexible arm;
the button comprises an elongate arm; and
the medicament delivery device is configured such that actuation of the button causes the elongate arm to deflect the flexible arm such that the protrusion engages the cooperating element to hold the needle cover in the retracted position.

27. The medicament delivery device of claim 25, wherein:
the resilient member comprises a flexible arm and a protrusion disposed on a free end of the flexible arm;
the button comprises an elongate arm;
the body comprises the cooperating element;
the flexible arm is movable between a first position, in which the protrusion engages the cooperating element to hold the needle cover in the retracted position, and a second position, in which the protrusion is disengaged from the cooperating element;
the flexible arm is biased to deflect from the second position to the first position;
the elongate arm is configured to hold the flexible arm in the second position prior to actuation of the button; and
the medicament delivery device is configured such that actuation of the button causes the elongate arm to release the flexible arm to deflect to the first position.

28. The medicament delivery device of claim 16, further comprising the syringe containing a medicament.

29. A medicament delivery device comprising:
a body configured to hold a syringe having a needle and containing a medicament;
a needle cover axially movable relative to the body between an extended position in which a distal end of the needle cover is distal to a distal end of the needle, and a retracted position in which the distal end of the needle is distal to the distal end of the needle cover; and
a member configured to releasably hold the needle cover in the retracted position against a force biasing the needle cover toward the extended position,
wherein the member is arranged at an outer circumferential surface of the body, and wherein the member is configured to be actuated by a user to move radially into the body from an initial position to an engaged position to releasably hold the needle cover.

* * * * *